(12) United States Patent
Sharma et al.

(10) Patent No.: US 11,678,658 B2
(45) Date of Patent: Jun. 20, 2023

(54) DEVICES, SYSTEMS, AND METHODS FOR MODELING OCULAR TRANSLAMINAR PRESSURE GRADIENTS

(71) Applicant: UNIVERSITY OF NORTH TEXAS HEALTH SCIENCE CENTER, Fort Worth, TX (US)

(72) Inventors: Tasneem Putliwala Sharma, Fort Worth, TX (US); Colleen Mary McDowell, Fort Worth, TX (US); Abbot Frederick Clark, Fort Worth, TX (US); Husain Lohawala, Fort Worth, TX (US)

(73) Assignee: UNIVERSITY OF NORTH TEXAS HEALTH SCIENCE CENTER, Ft. Worth, TX (US)

( * ) Notice: Subject to any disclaimer, the term of this patent is extended or adjusted under 35 U.S.C. 154(b) by 1054 days.

(21) Appl. No.: 16/395,610

(22) Filed: Apr. 26, 2019

(65) Prior Publication Data
US 2019/0327958 A1    Oct. 31, 2019

Related U.S. Application Data

(60) Provisional application No. 62/663,751, filed on Apr. 27, 2018.

(51) Int. Cl.
*A01N 1/02* (2006.01)
*B01L 3/00* (2006.01)
*G01N 33/50* (2006.01)

(52) U.S. Cl.
CPC ............ *A01N 1/0247* (2013.01); *B01L 3/502* (2013.01); *G01N 33/5088* (2013.01);
(Continued)

(58) Field of Classification Search
CPC ..... A01N 1/0247; A01N 1/0263; B01L 3/502; B01L 2300/042; B01L 2300/0609;
(Continued)

(56) References Cited

U.S. PATENT DOCUMENTS

| | | | | |
|---|---|---|---|---|
| 3,941,567 A | * | 3/1976 | Combaz | ................ G01N 30/12 359/398 |
| 2002/0178790 A1 | * | 12/2002 | Swersey | ............ G01N 15/0826 73/38 |
| 2003/0087292 A1 | * | 5/2003 | Chen | .................... C12Q 1/6834 435/6.12 |

FOREIGN PATENT DOCUMENTS

| | | | | |
|---|---|---|---|---|
| WO | WO-0049447 A1 | * | 8/2000 | ............. B01L 3/508 |
| WO | WO-2006091729 A2 | * | 8/2006 | ............. A61K 38/53 |
| WO | WO-2016004171 A1 | * | 1/2016 | ............... B01L 3/52 |

OTHER PUBLICATIONS

Berdahl, et al., "Cerebrospinal Fluid Pressure is Decreased in Primary Open-Angle Glaucoma," Opthamology, 115(5): 763-768, 2008.
(Continued)

*Primary Examiner* — Benjamin R Whatley
*Assistant Examiner* — Jacqueline Brazin
(74) *Attorney, Agent, or Firm* — Norton Rose Fulbright US LLP

(57) ABSTRACT

The present disclosure relates to devices, systems, and methods for modeling ocular translaminar pressure gradients ex vivo. A first fluid pressure level can be applied to a first side of a wall of donor eye cup (e.g., a posterior human eye cup) to simulate intracranial pressure (ICP), for example around the optical nerve head (ONH), and a second fluid pressure level can be applied to a second side of the wall of the donor eye cup to simulate intraocular pressure (IOP).

(Continued)

These devices, systems, and methods are unique in that they allow ex vivo modeling of dynamic changes in translaminar pressure gradients.

20 Claims, 23 Drawing Sheets

(52) U.S. Cl.
CPC . *B01L 2300/042* (2013.01); *B01L 2300/0609* (2013.01); *B01L 2300/0627* (2013.01); *B01L 2300/0809* (2013.01); *B01L 2300/0832* (2013.01); *B01L 2300/0858* (2013.01); *B01L 2300/14* (2013.01); *B01L 2400/0487* (2013.01)

(58) Field of Classification Search
CPC ..... B01L 2300/0627; B01L 2300/0809; B01L 2300/0832; B01L 2300/0858; B01L 2300/14; B01L 2400/0487; G01N 33/5088
USPC .......................................................... 435/1.2
See application file for complete search history.

(56) References Cited

OTHER PUBLICATIONS

Berdahl, et al., "Intracranial Pressure in Primary Open Angle Glaucoma, Normal Tension Glaucoma, and Ocular Hypertension: A Case-Control Study," Investigative Ophthalmology & Visual Science, 49(12): 5412-5418, 2008.
Feola, et al., "Deformation of the Lamina Cribrosa and Optic Nerve Due to Changes in Cerebrospinal Fluid Pressure," Investigative Ophthalmology & Visual Science, 58(4): 2070-2078, 2017.
Fleischman, "The Role of Cerebrospinal Fluid Pressure in Glaucoma and Other Ophthalmic Diseases, A Review," Saudi Journal of Ophthalmology, 27(2): 97-106, 2013.
Morgan, et al., "Optic Disc Movement with Variations in Intraocular and Cerebrospinal Fluid Pressure," Investigative Ophthalmology & Visual Science, 43(10): 3236-3242, 2002.
Morgan, et al., "The Correlation Between Cerebrospinal Fluid Pressure and Retrolaminar Tissue Pressure," Investigative Ophthalmology & Visual Science, 39(8): 1419-1428, 1998.
Morgan, et al., "The Influence of Cerebrospinal Fluid Pressure on the Lamina Cribosa Tissue Pressure Gradient," Investigative Opthalmology & Visual Science, 36(6): 1163-1172, 1995.
Yang, et al., "Optic Neuropathy Induced by Experimentally Reduced Cerebrospinal Fluid Pressure in Monkeys," Investigative Ophthalmology & Visual Science, 55(5): 3067-3073, 2014.

* cited by examiner

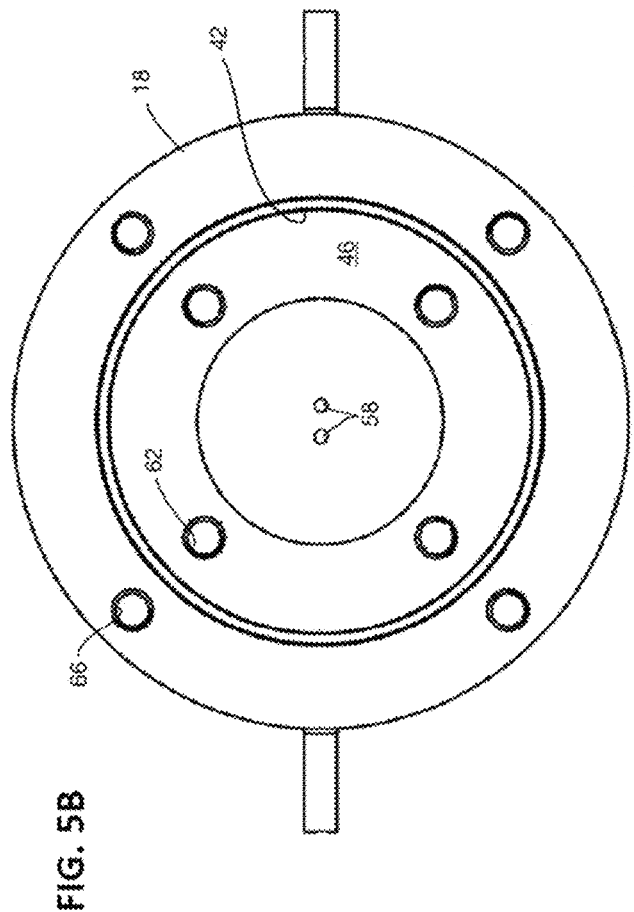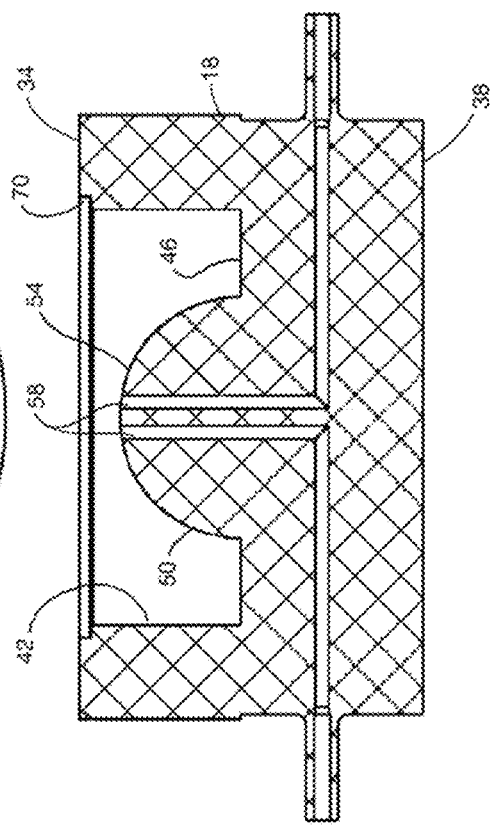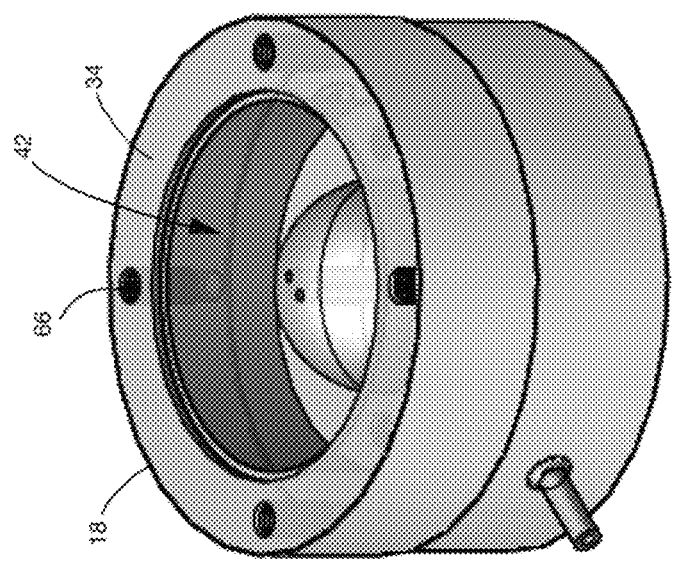
FIG. 5B
FIG. 5C
FIG. 5A

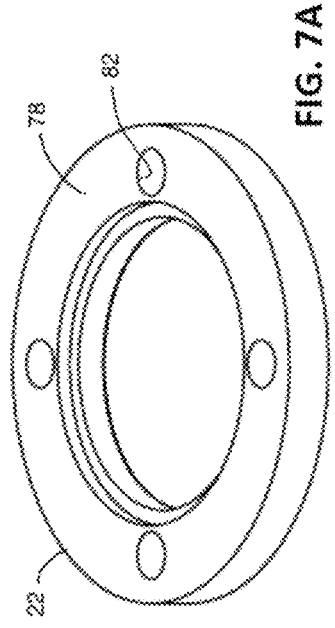
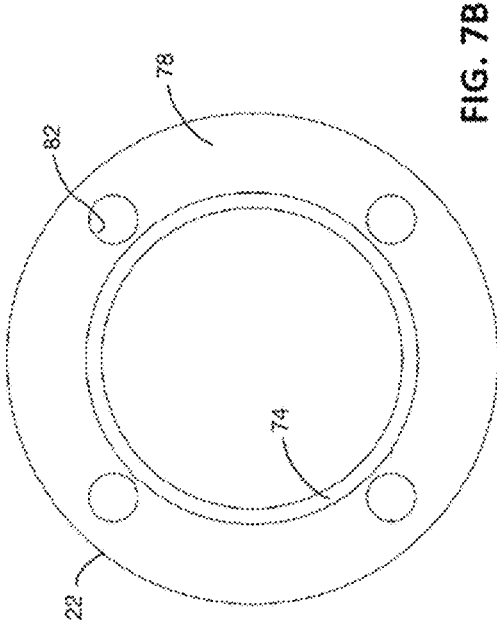
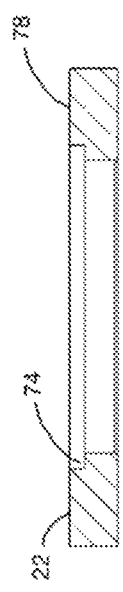
FIG. 7A  FIG. 7B  FIG. 7C
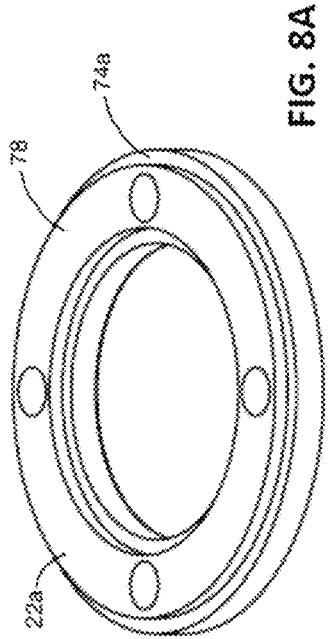
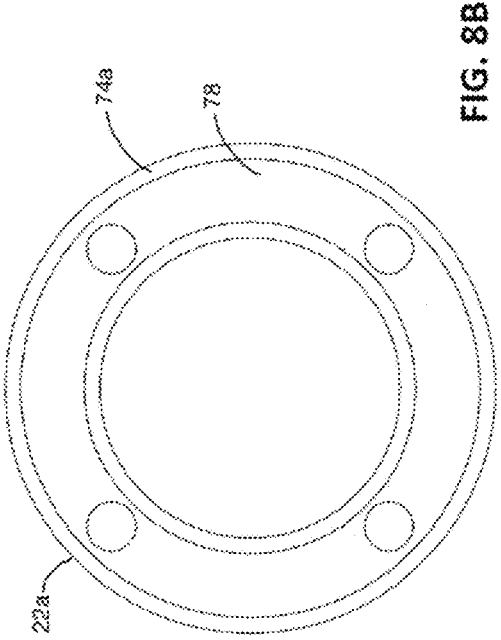
FIG. 8A  FIG. 8B  FIG. 8C

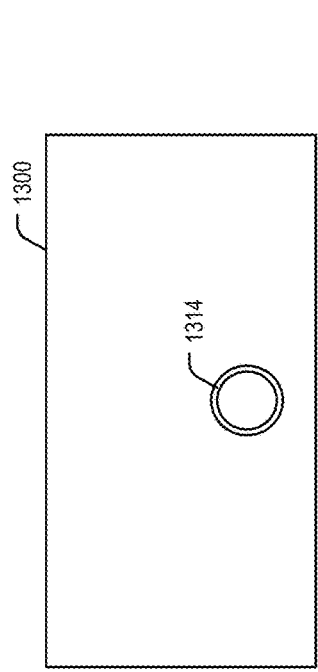
FIG. 13B
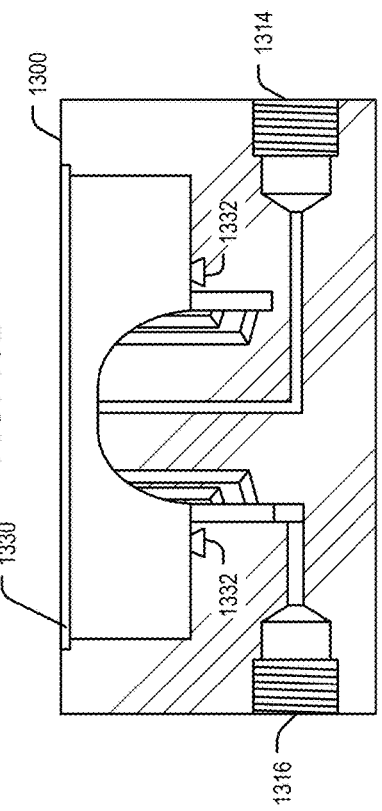
FIG. 13D
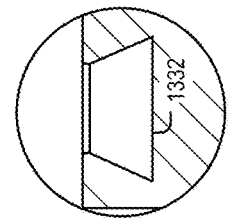
FIG. 13E
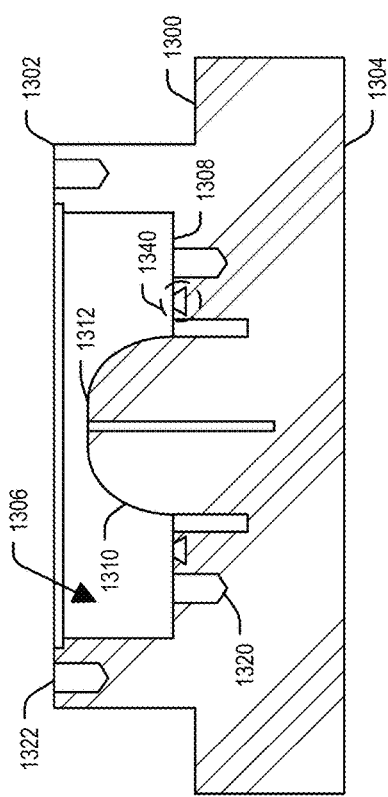
FIG. 13A
FIG. 13C

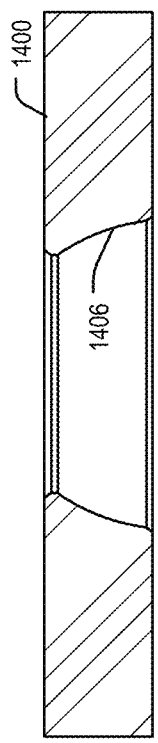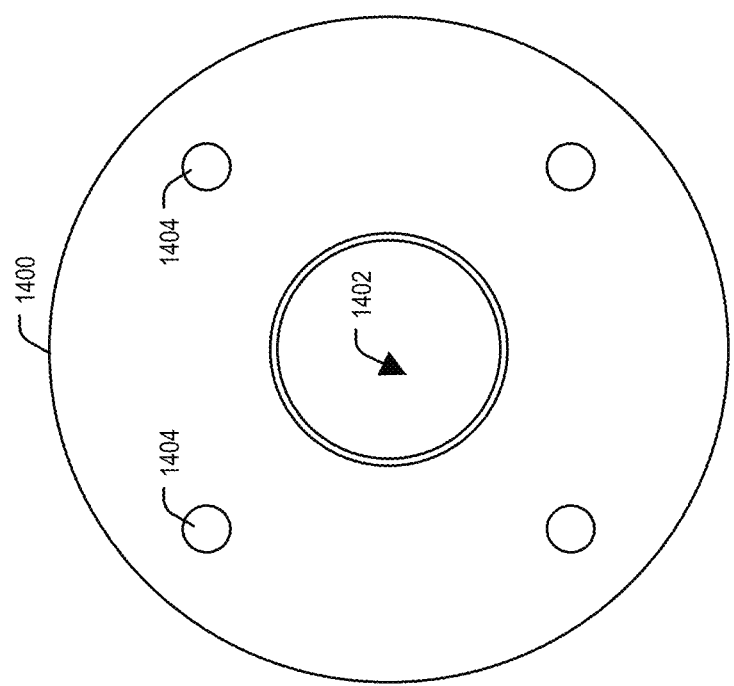

DEVICES, SYSTEMS, AND METHODS FOR MODELING OCULAR TRANSLAMINAR PRESSURE GRADIENTS

CROSS-REFERENCE TO RELATED APPLICATIONS

This application claims the benefit of priority of U.S. Provisional Patent Application No. 62/663,751 filed Apr. 27, 2018, the entire content of which is specifically incorporated herein by reference without disclaimer.

FIELD OF THE DISCLOSURE

The present invention relates generally to the ocular health; and more particularly, but not by way of limitation, to devices, systems, and methods for ex vivo modeling and/or study of translaminar pressure gradients on the posterior human eye cup and optic nerve head.

BACKGROUND

Current glaucoma models generally consider only the effects of intraocular pressure (IOP) in glaucoma. It has been suggested that cerebrospinal fluid pressure (CSFp) may also play a role in the death of retinal ganglion cells (retinal neurons) in glaucoma. Besides intraocular pressure, the optic nerve is exposed to intracranial pressure (ICP) as it is surrounded by CSF in the subarachnoid space. The lamina cribosa (LC) region separates these pressurized chambers. The average normal IOP ranges from 10-21 mm Hg, and the average normal ICP ranges from 10-15 mm Hg. The pressure difference between these two chambers is called the translaminar pressure gradient. There is evidence to indicate that ICP is lower almost 5 mm Hg in glaucoma patients compared to normal individuals, thereby causing increased translaminar pressure and playing a crucial role in glaucoma pathogenesis.

The first studies for the relationship between ICP and IOP were performed in canines by Morgan et al. [1], [6], [8]. Multiple additional studies were then performed to study, and correlations were developed for ICP in human glaucoma patients through retrospective studies [2], [3], [7]. These results were validated by animal studies performed on non-human primates [9]. In a canine model it was demonstrated that changes in IOP and ICP can result in large displacements of the optic disc. More-recent models include studying ICP with porcine eyes (Feola et al., 2017 [4], [5]) through blunt cannulation of the optic nerve of porcine eyes that are glued to a platform. Elevating IOP in porcine eyes has shown increased principal strain within the LC region and retrolaminar neural tissue, and increased strain on the retinal ganglion cells (RGCs). The LC region is believed to contribute to axonal transport blockage and loss of neurons.

Even in non-human primates, current procedures are invasive and time consuming. Examples of current models include: blunt cannulation of the optic nerve (porcine eyes), MII image scans (canine models), intracranial pressure-sensing devices implanted in the burr hole epidurally (monkeys), and performing invasive lumbar punctures in patients. But these do not permit dynamic modulations of ICP in human eyes.

SUMMARY

The present devices are configured to receive a donor eye cup (e.g., a posterior human eye cup) and form a posterior chamber in which the optic nerve head (ONH) is positioned face down and the optic nerve on the opposite side of the eye cup, permitting independent simulation and modulation over time of ICP and IOP on either side of the eye cup. While the device may be particularly beneficial for studying human eye cups, it can also be configured to study porcine, bovine, canine, and/or feline eye cups. This allows the study of the effects of static and/or dynamically changing translaminar pressure gradients that could arise in various insults including from glaucoma. Additionally, the present devices, systems, and methods can be used to study various other effects of translaminar pressure gradients, such as, for example, anatomical changes (e.g., deformation of the optic nerve) that may arise in posterior eye tissue of astronauts after space travel or that in traumatic brain injury patients with abnormal ICP. Testing of the present devices, systems, and methods have shown an ability to culture a donor human posterior eye cup and regulate pressure for 7 days.

The present devices, systems, and methods are unique in that they enable ex vivo human modeling of IOP and ICP painlessly and without the use of lumbar punctures and, as a result, offers the potential of a platform for developing neurodegenerative therapeutics that focus on translaminar pressure as a mechanism of degeneration. Even though the effects of IOP have been well-studied, relatively minimal research has been performed on abnormal translaminar pressure changes. Understanding pressure-related neurodegenerative changes should be beneficial for preventing visual neuronal RGC death.

Additionally, the present devices, systems, and methods enable study of Spaceflight-Associated Neuro-Ocular Syndrome (SANS). The ex vivo human model can be used for classification of cellular and functional modifications that occur due to chronic mild elevation of ICP under conditions of microgravity. They devices and systems described herein can be used not only on the ground, under conditions of zero gravity but are cost-effective enough to be transported to in-flight testing missions. This provides not only a human model as a basis for testing, but a model that can be utilized to test countermeasures like artificial gravity and to identify therapies and treatments that can directly save RGCs from neurodegeneration as observed in SANS. The devices, systems, and methods described herein may enable the provision of medicine through patient cells and allow effective translation of the research to the clinic. Further, therapies can be efficaciously tested in vitro in a cost-effective manner with the capacity to be relatable to living individuals.

Some of the present devices (e.g., for modeling ocular translaminar pressure gradients) comprise: a base, an annular retainer, and a lid. In some configurations, the base has a first end and a second end, and defines: a recess extending from the first end to a bottom defined between the first and second ends; and a protrusion extending upward from the bottom of the recess to an upper end disposed between the bottom of the recess and the first end of the base, the upper end sized to receive a donor eye cup (e.g., a human posterior donor eye cup) over the upper end; where the base defines at least one fluid port extending through the upper end of the protrusion. The base may define two fluid ports extending through the upper end of the protrusion, and the lid defines two fluid ports in fluid communication with the chamber. Alternatively, the base may define a first fluid port extending through the upper end of the protrusion and a second fluid port extending below the upper end of the protrusion, and the lid may define two fluid ports in fluid communication with the chamber. The distal end of the protrusion of the base may be hemispherical, and/or the protrusion of the base may have a circular cross-section. In some configurations, the recess around the protrusion defines an annular space sized to receive the retainer.

In some configurations, the annular retainer is annular and configured to fit around and over the protrusion and to be coupled to the base to secure the donor eye cup between the annular retainer and the base and to seal the interface between the donor eye cup and the protrusion. The annular retainer may define one or more annular grooves each configured to receive an O-ring.

In some configurations, the lid has a first side, a second side configured to face the first end of the base, and an annular sidewall on the second side, the annular sidewall defining a chamber and having a distal end that encircles an open end of the chamber, the distal end of the annular sidewall configured such that when the lid is secured relative to the first end of the base and a donor eye cup is secured to the protrusion of the base, the distal end of the annular sidewall extends into the recess of the base to secure the donor eye cup between the annular sidewall and the protrusion and seal the interface between the annular sidewall and the donor eye cup, where the lid defines at least one fluid port in fluid communication with the chamber. In some configurations, an inner diameter of the annular sidewall of the lid is smaller than a diameter of the protrusion of the base and, optionally, when the lid is secured relative to the base, a minimum distance between the upper end of the protrusion of the base and the distal end of the annular sidewall of the lid may be greater than zero but smaller than an average thickness of a wall of an adult human donor eye cup.

In some configurations, the lid is substantially square-shaped and the base is substantially square-shaped. In some configurations, the chamber includes an insert disposed at a particular angle from an axis through the protrusion. The particular angle may be between substantially 6 degrees and substantially 10 degrees.

Some of the present systems (e.g., for modeling ocular translaminar pressure gradients) comprise: one of the present devices; a first source of fluid pressure in fluid communication with the at least one fluid port of the base; and a second source of fluid pressure in fluid communication with the at least one fluid port of the lid. In some configurations, the base defines two fluid ports extending through the upper end of the protrusion, and the lid defines two fluid ports in fluid communication with the chamber, the first source of fluid pressure is coupled to a first one of the fluid ports of the base, the second source of fluid pressure is coupled to a first one of the fluid ports of the lid, and the system may further comprise: a first pressure transducer coupled to a second one of the fluid ports of the base; and a second pressure transducer coupled to a second one of the fluid ports of the lid.

Some of the present methods (e.g., for modeling ocular translaminar pressure gradients) comprise, in one of the present devices or systems having a donor eye cup secured between the retainer and the base and the lid coupled to the base: adjusting a fluid pressure gradient between a first fluid pressure in the one or more fluid ports of the base and a second fluid pressure in the one or more fluid ports of the lid, and thereby adjusting a corresponding fluid pressure gradient between the first fluid pressure on one side of the donor eye cup between the donor eye cup and the protrusion and the second fluid pressure on the other side of the donor eye cup in the chamber of the lid. Some implementations of the present methods may further comprise: varying the fluid pressure gradient over time.

In some implementations of the present methods, adjusting the fluid pressure involves adjusting the relative heights of fluid reservoirs respectively coupled to the fluid ports of the base and lid.

In implementations of the present methods where the base defines two fluid ports extending through the upper end of the protrusion, and the lid defines two fluid ports in fluid communication with the chamber, the first source of fluid pressure may be coupled to a first one of the fluid ports of the base, the second source of fluid pressure may be coupled to a first one of the fluid ports of the lid, and the method may further comprise: measuring the first fluid pressure with a first pressure transducer coupled to a second one of the fluid ports of the base; and measuring the second fluid pressure with a second pressure transducer coupled to a second one of the fluid ports of the lid.

As used herein, various terminology is for the purpose of describing particular implementations only and is not intended to be limiting of implementations. For example, as used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term). The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified—and includes what is specified; e.g., substantially 90 degrees includes 90 degrees and substantially parallel includes parallel—as understood by a person of ordinary skill in the art. In any disclosed embodiment, the term "substantially" may be substituted with "within [a percentage] of" what is specified, where the percentage includes 0.1, 1, 5, and 10 percent; and the term "approximately" may be substituted with "within 10 percent of" what is specified.

The terms "comprise" and any form thereof such as "comprises" and "comprising," "have" and any form thereof such as "has" and "having," and "include" and any form thereof such as "includes" and "including" are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any implementation of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. Additionally, it will be understood that the term "wherein" may be used interchangeably with "where."

Further, a device or system that is configured in a certain way is configured in at least that way, but it can also be configured in other ways than those specifically described. Aspects of one example may be applied to other examples, even though not described or illustrated, unless expressly prohibited by this disclosure or the nature of a particular example. Some details associated with the aspects described above and others are described below.

Some details associated with the aspects are described above, and others are described below. Other implementations, advantages, and features of the present disclosure will become apparent after review of the entire application, including the following sections: Brief Description of the Drawings, Detailed Description, and the Claims.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. Views in the figures are drawn to scale, unless otherwise noted, meaning the sizes of the depicted elements are accurate relative to each other for at least the embodiment in the view.

FIGS. 5A, 5B, and 5C depict perspective, top, and cross-sectional side views, respectively, of an example of a base of the device of FIG. 1.

FIGS. 7A, 7B, and 7C depict perspective, top, and cross-sectional side views, respectively, of a first example of a retainer ring of the device of FIG. 1.

FIGS. 8A, 8B, and 8C depict perspective, top, and cross-sectional side views, respectively, of a second example of a retainer ring for the present devices.

FIGS. 13A, 13B, 13C, and 13D depict top, side, first cross-sectional side, and second cross-sectional side views, respectively, of another example of a base of one of the present devices.

FIG. 13E depicts an expanded view of a portion of FIG. 13C.

FIGS. 14A, 14B, and 14C depict top, cross-sectional side, and side views, respectively, of another example of a retainer ring of one of the present devices.

DETAILED DESCRIPTION OF ILLUSTRATIVE EMBODIMENTS

At a high level, the present devices are configured to secure a donor eye cup—e.g., a posterior human donor eye cup—such that a pressure gradient across the thickness of the wall of the eye cup can be adjusted ex vivo, for example to simulate a translaminar pressure gradient between IOP and ICP.

Figure 1:
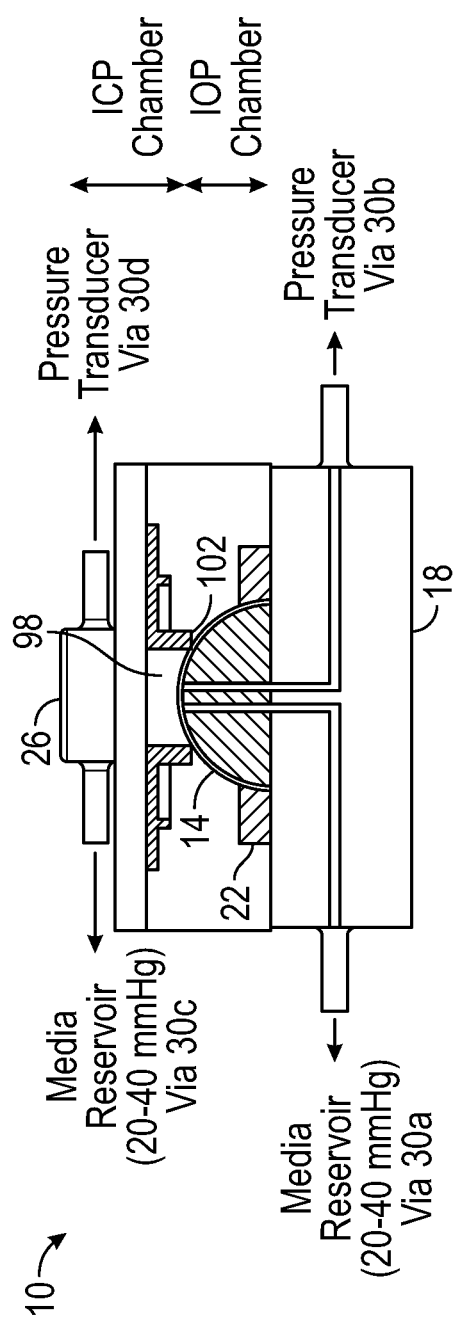
FIG. 1 depicts a partially cutaway side view of wireframe model of one example of the present devices.
Figure 2:
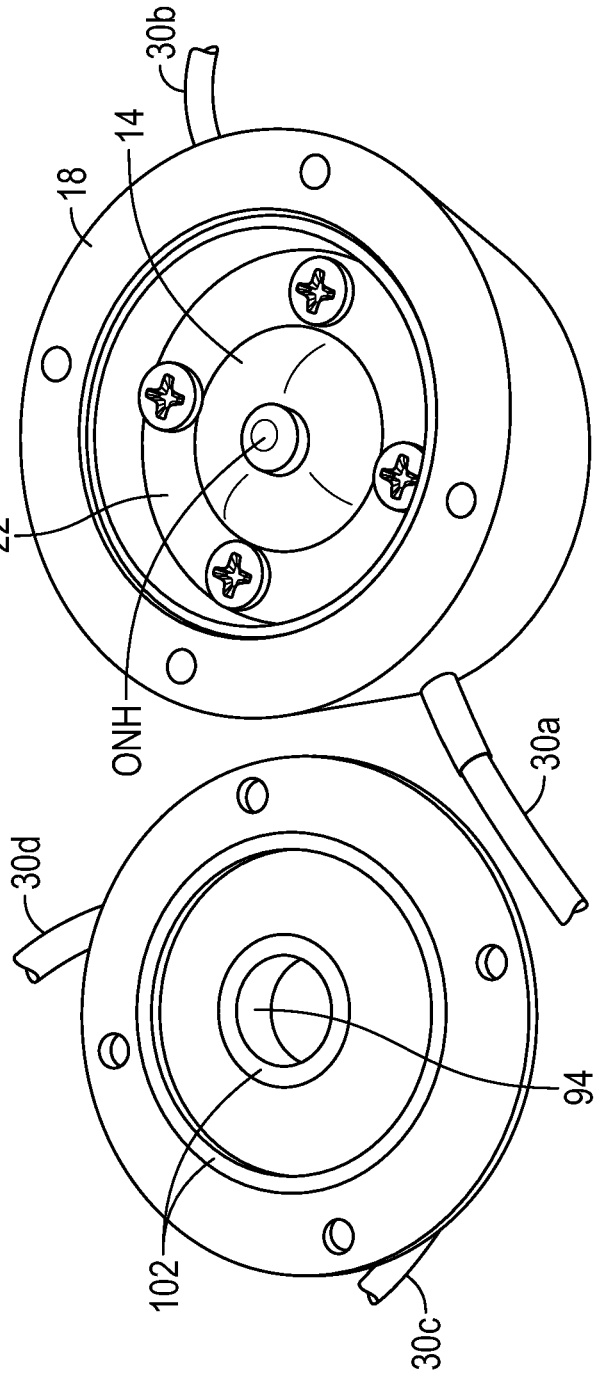
FIG. 2 depicts a perspective view of a partially disassembled prototype of the device of FIG. 1, shown with a human posterior eye cup secured in a base by a retainer ring and a lid separated from the base.

Referring now to the drawings, and more particularly to FIGS. 1-7C, shown there and designated by the numeral 10 is an example of the present devices. More particularly, FIG. 1 depicts a partially cutaway side view of wireframe model of one example of the present devices; FIG. 2 depicts a perspective view of a partially disassembled prototype 10a of device 10, shown with a donor eye cup 14 (e.g., human posterior eye cup) secured in a base 18 by a retainer 22, and a lid 26 separated from the base; FIG. 3A shows a perspective view of prototype 10a, shown with conduits 30a, 30b, 30c, 30d connecting respective fluid ports to fluid reservoirs (FIG. 3B) and pressure transducers (not shown); FIGS. 4A and 4B show perspective views of a second prototype 10b of device 10; FIGS. 5A-5C show various views of base 18 of device 10; FIGS. 6A-6C show various views of lid 26 of device 10; and FIGS. 7A-7C show various views of retainer 22 (e.g., an annular retainer) of device 10.

As shown in detail in FIGS. 5A-5C, base 18 has a first end 34 and a second end 38, and defines a recess 42 extending from first end 34 to a bottom 46 defined between the first and second ends. Base 18 also defines a protrusion 50 extending upward from bottom 46 to an upper end 54 disposed between bottom 46 and first end 34. Upper end 54 of the protrusion is sized to receive a donor eye cup (e.g., 14) over the upper end. For example, in the depicted configuration, protrusion 50 has a circular cross section, upper end 54 (and, in this configuration the entirety of protrusion 50) is hemispherical, and each of protrusion 50 and upper end 54 has a diameter about equal to or slightly smaller than an average diameter of a donor eye cup with which the device is intended to be used (and/or of an actual diameter of a donor eye cup with which the device is intended to be used). In the depicted configuration, recess 46 has a circular cross-sectional shape which, together with protrusion 50, defines an annular space around the protrusion, which annular space is sized to receive the retainer (22) to secure a donor eye cup. The base also defines at least one fluid port extending through the upper end of the protrusion to enable fluid pressure to be communicated to the space between the donor eye cup and the upper end to simulate intraocular pressure (IOP). For example, in the depicted configuration, base 18 defines two fluid ports 58 extending through upper end 54 of protrusion 50.

In the configuration shown, base 18 also defines a plurality of threaded retainer holes 62 and a plurality of threaded lid holes 66, for securing retainer 22 and lid 26, respectively, to base 18. In other embodiments, the base, retainer, and lid may be configured to be secured to one another in any suitable way and/or with any suitable structure. For example, the inner wall of base 18 that defines the recess may be provided with female threads, and the corresponding outer surface of retainer 22 may be provided with male threads, such that the retainer can be rotated into the recess such that the threads secure the retainer relative to the body.

Additionally, in the depicted configuration, base 18 defines a groove or notch 70 around the upper perimeter of recess 42, which groove or notch 70 is configured to receive an O-ring or seal to assist with sealing the interface between lid 26 and base 18 when the lid is coupled to the base.

As shown in detail in FIGS. 7A-7C, retainer 22 is configured to fit around and over protrusion 50 and to be coupled to base 18 to secure the donor eye cup (e.g., 14) between the retainer and the base and to seal the interface between the donor eye cup and the protrusion. For example, in the depicted configuration, retainer 22 is provided with an annular shape defining a central opening having a diameter that is about equal to or slightly larger than the outer diameter of protrusion 50 at the point at which retainer 22 is secured to base 18. By way of example, in some embodiments, the difference in these diameters may be such that a space between the protrusion and the portion of retainer 22 that is closest to protrusion 50 is smaller than an average thickness of a corresponding portion of a wall of a donor eye cup (and/or smaller than the thickness of the corresponding portion of the wall of an actual donor eye cup) with which the device is intended to function. In the embodiment shown, retainer 22 defines a groove or notch 74 on a lower side 78 of the retainer, which groove or notch is configured to receive an O-ring or seal to assist with sealing the interface between retainer 22 and base 18 when the retainer is coupled to the base. Because groove or notch 74 is on the lower side of retainer, an O-ring or seal in the groove or notch is compressed between the retainer and the base to fill any imperfections in the interface as the retainer is secured to the base. In some implementations, a portion of a donor eye cup may extend to the interface between the O-ring and protrusion 50, such that the O-ring also assist with securing the donor eye cup relative to the protrusion. In the depicted configuration, retainer 22 also defines a plurality of holes 82 configured to be aligned with threaded retainer holes 62 in base 18 such that the retainer can be secured to the base with screws or bolts.

Figure 6A:
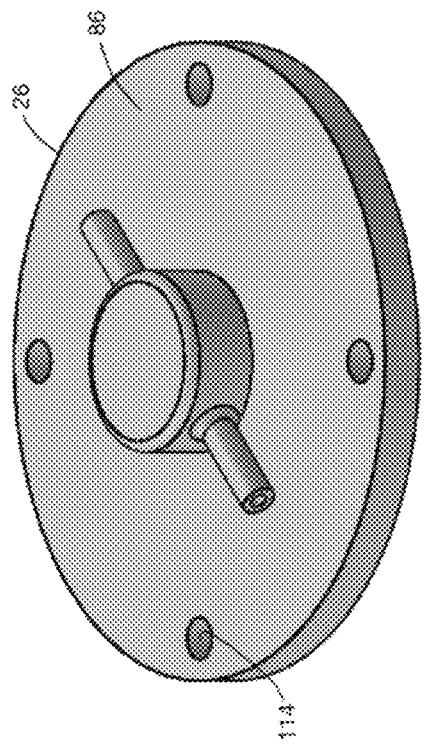
FIGS. 6A, 6B, and 6C depict perspective, top, and cross-sectional side views, respectively, of an example of a lid of the device of FIG. 1.
Figure 6B:
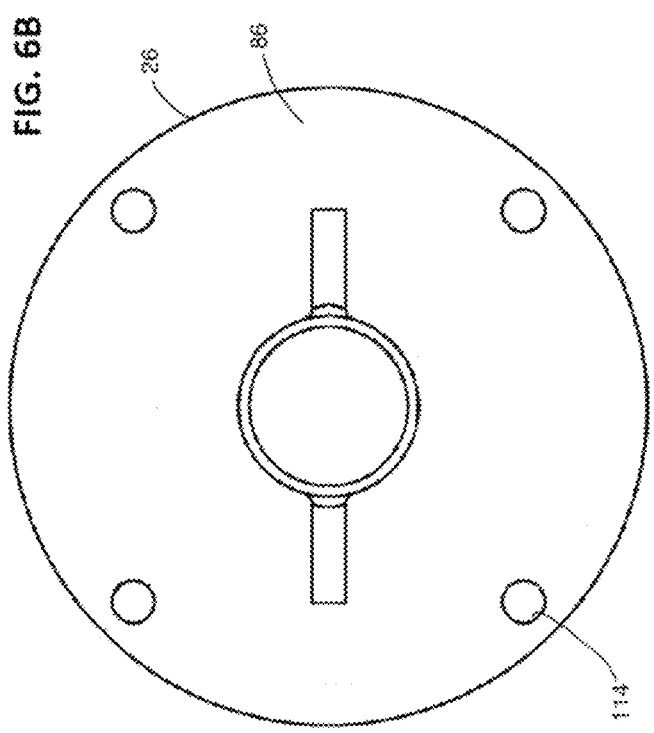
Figure 6C:
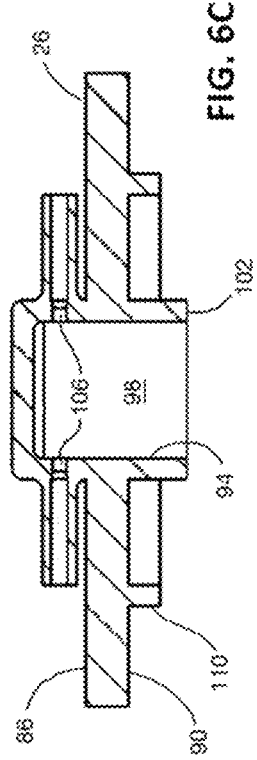

As shown in detail in FIGS. 6A-6C, lid 26 has a first side 86, a second side 90 configured to face first end 34 of base 18, and an annular sidewall 94 on the second side. As shown, annular sidewall 94 defines a chamber 98 and has a distal end 102 that encircles an open end of the chamber. Distal end 102 of annular sidewall 94 is configured such that when lid 26 is secured relative to first end 34 of base 18 and a donor eye cup (e.g., 14) is secured to the protrusion of the base (as illustrated in FIGS. 1 and 2), distal end 102 of annular sidewall 94 extends into recess 42 of the base to secure the donor eye cup between the annular sidewall (94) and the protrusion (50) and to seal the interface between annular sidewall 94 and the donor eye cup. This seal can be provided any of various ways. For example, in the embodiments shown, the inner diameter of annular sidewall 94 at distal end 102 is smaller than the maximum outer diameter of protrusion 50, and distal end 102 extends only part way down the hemispherical upper end of protrusion 50 to a point at which a minimum distance between upper end 54 of protrusion 50 and distal end 102 of annular sidewall 94 of the lid is smaller than an average thickness of a wall of a donor eye cup (and/or an actual thickness of a corresponding portion of a donor eye cup) with which device 10 is intended to be used. In the depicted configuration, the lid and base are therefore configured to pinch the donor eye cup between protrusion 50 and distal end 102 of annular sidewall 94 to create the seal between distal end 102 and the donor eye cup. As a result, chamber 98 can be pressurized to simulate intracranial pressure (ICP) on the outer side of the donor eye cup (with the optical nerve head (ONH)). The lid also defines at least one fluid port in fluid communication with chamber 98 to enable fluid pressure to be communicated to the chamber 98 to simulate IOP. For example, in the depicted configuration, lid 26 defines two fluid ports 106 in fluid communication with chamber 98.

In the configuration shown, lid 26 also defines an outer annular sidewall 110 on second side 90, which sidewall 110 has an outer diameter about equal to or just smaller than the inner wall of base 18 defining recess 42. The outer surface of outer annular sidewall 110 therefore cooperates with notch or groove 70 of base 18 to compress an O-ring or seal in that notch or groove to help seal the interface between the lid and the base. In the depicted configuration, lid 26 also defines a plurality of holes 114 configured to be aligned with threaded lid holes 66 in base 18 such that the lid can be secured to the base with screws or bolts.

FIGS. 8A-8C show various views of a second example of a retainer 22a for use with device 10. Retainer 22a is substantially similar to retainer 22, with the exception that retainer 22a defines a second groove or notch 74a on lower side 78 of the retainer, which groove or notch is configured to receive an O-ring or seal to assist with sealing the interface between the outer perimeter of retainer 22a and base 18 when the retainer is coupled to the base. Because second groove or notch 74a is also on the lower side of retainer, an O-ring or seal in the groove or notch is compressed between the retainer and the base to fill any imperfections in the interface as the retainer is secured to the base.

Figure 9A:
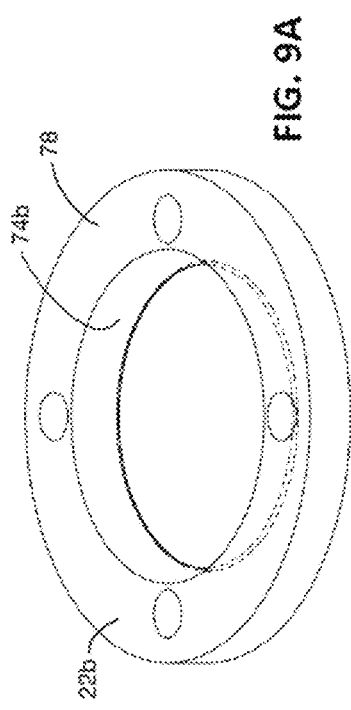
FIGS. 9A, 9B, and 9C depict perspective, top, and cross-sectional side views, respectively, of a third example of a retainer ring for the present devices.
Figure 9B:
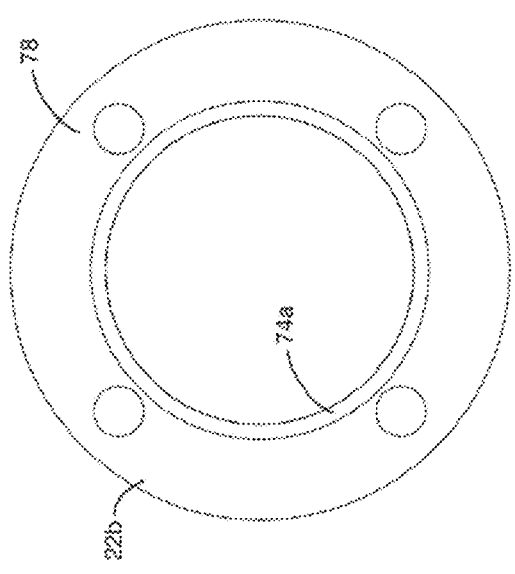
Figure 9C:
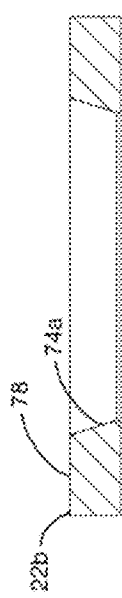

FIGS. 9A-9C show various views of a third example of a retainer 22b for use with device 10. Retainer 22b is substantially similar to retainer 22, with the exception that retainer 22b does not define any grooves or notches (e.g., 74a) on lower side 78 of the retainer, and instead its interior wall 74b defining the central opening is angled so that the central opening is larger at the lower side 78 of the retainer than at the top. This angle, and the resulting narrower top of the central opening, assists with securing the donor eye cup by pinching the donor eye cup wall between retainer 22b and protrusion 50 of the base.

The present devices can be 3D printed from epoxy resin, molded and/or machined from various polymers, and/or machined from various metals such as stainless steel. Depending on the material used, the components of the present devices may be sterilized via autoclave, ethylene oxide, and/or the like.

Figure 3B:
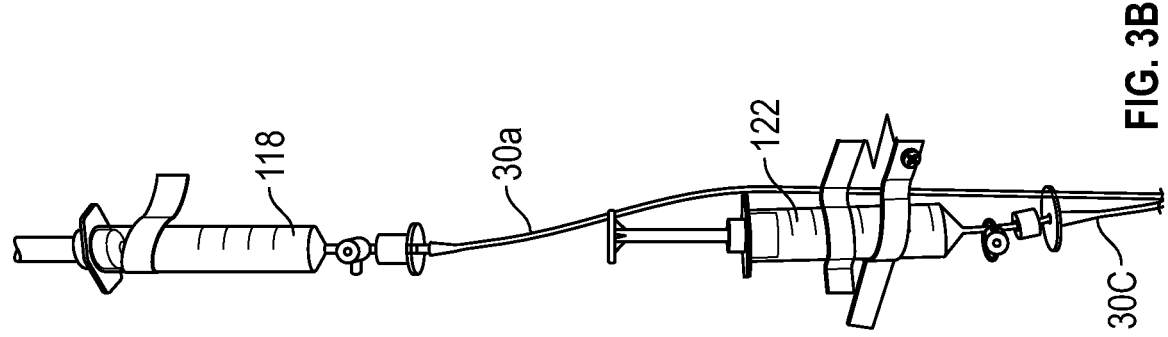
FIG. 3B depicts a perspective view of fluid reservoirs used with the prototype of FIG. 2 and FIG. 3A.
Figure 3A:
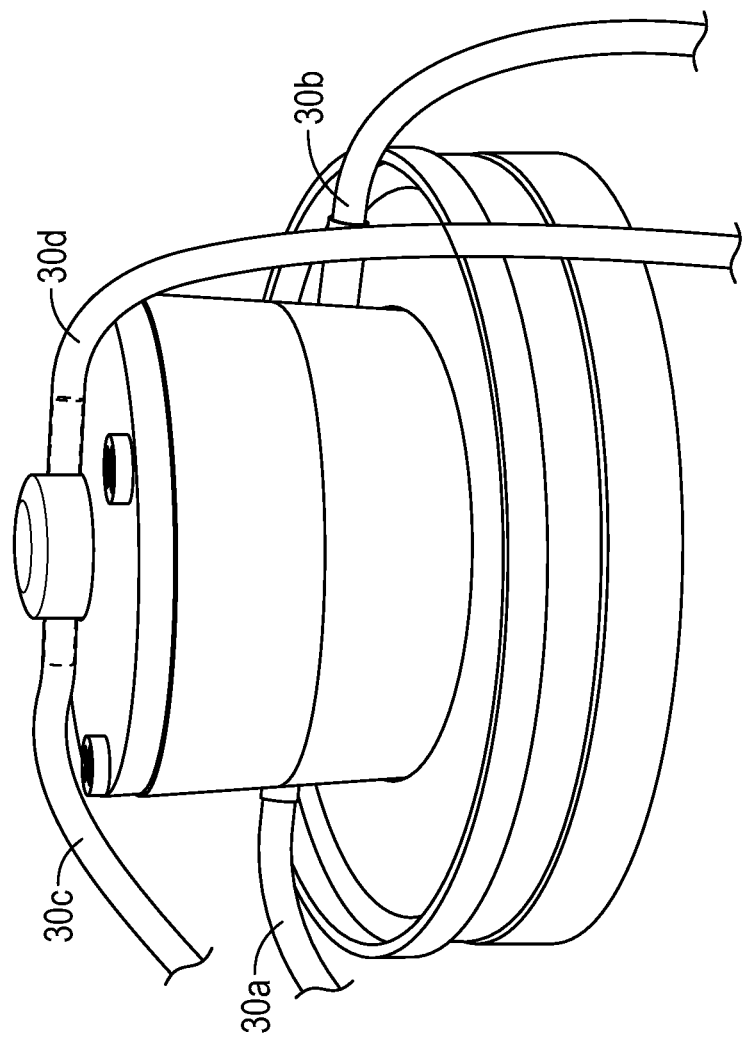
FIG. 3A depicts a perspective view of the prototype of FIG. 2, shown with conduits connecting respective ports to fluid reservoirs and pressure transducers.
Figure 4A:
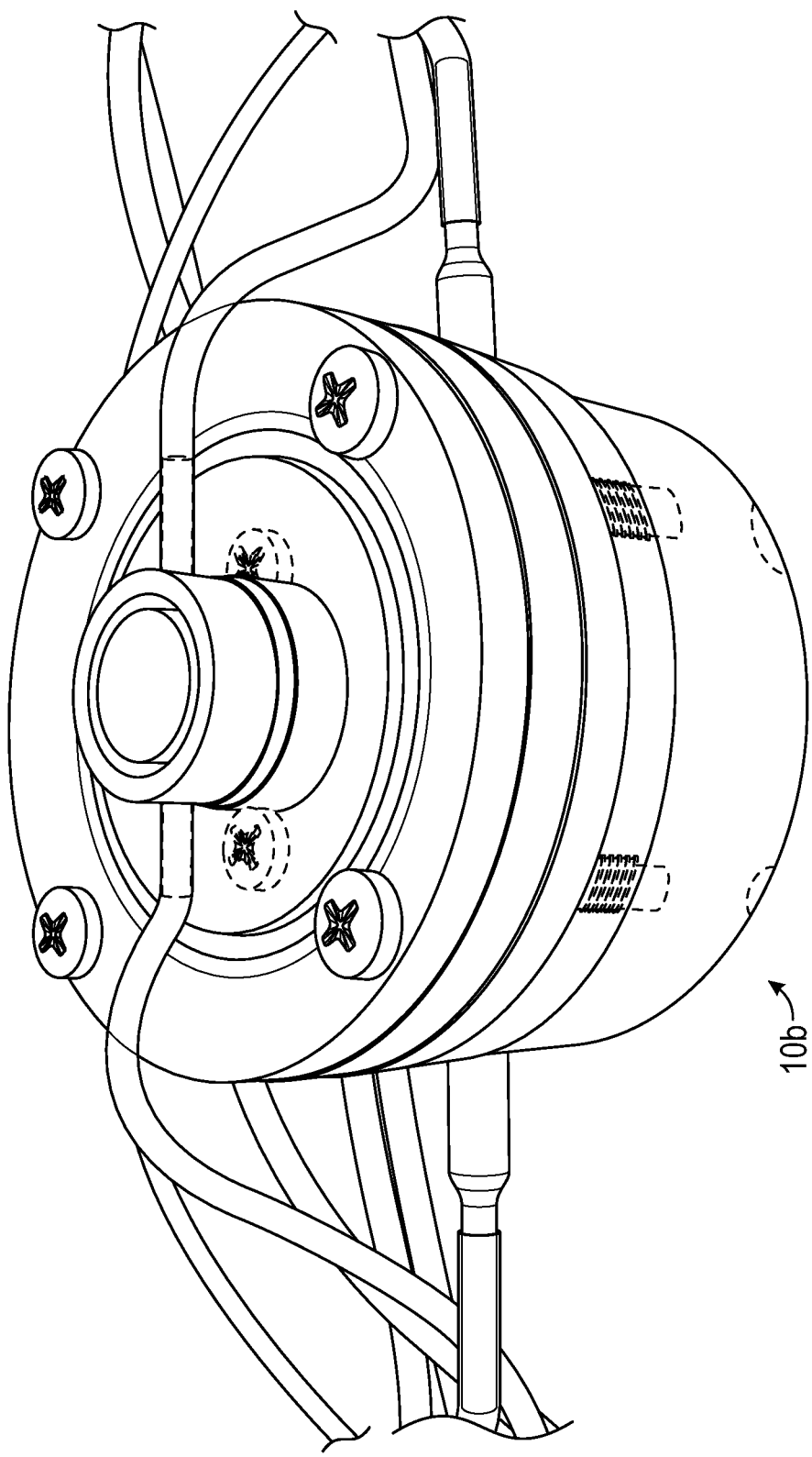
FIGS. 4A and 4B depict perspective views of a second prototype of the device of FIG. 1.
Figure 4B:
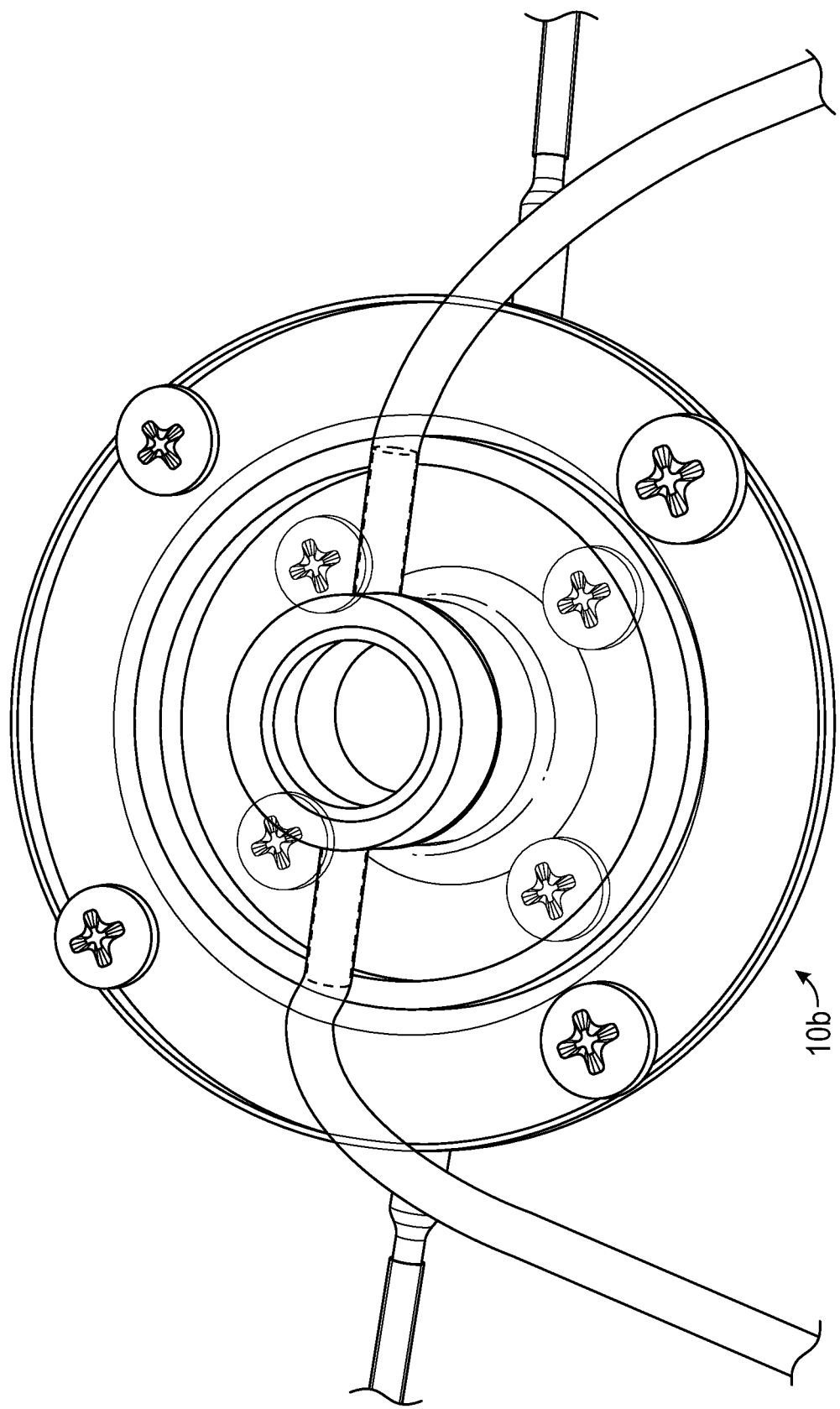

As shown in more detail in FIGS. 3A-3B, the present systems for modeling ocular translaminar pressure gradients can comprise a device 10 (e.g., prototype 10a), a first source of fluid pressure 118 in fluid communication with a fluid port of base 18; and a second source of fluid pressure 122 in fluid communication with a fluid port of the lid. For example, in the depicted configuration, first source of fluid pressure 118 comprises a syringe disposed a distance above device 10 and coupled to one of fluid ports 58 of the base by conduit 30a, and second source of fluid pressure 122 comprises a syringe disposed a distance above device 10 but below syringe 118 and coupled to one of fluid ports 106 of lid 26 via conduit 30c. In this configuration, the magnitude of the difference in elevation between syringes 118 and 122 determines the pressure gradient across the donor eye cup 14, and the pressure gradient can be increased by increasing the elevation of syringe 118 or reducing the elevation of syringe 122. In this configuration, a first pressure sensor (e.g., transducer) can be coupled to a second one of fluid ports 58 of base 18 via conduit 30b; and a second pressure sensor (e.g., transducer) can be coupled to a second one of fluid ports 106 of lid 26 via conduit 30d. In other embodiments, the respective fluid pressure sources can comprise perfusion pumps that allow the maintenance of a given pressure for fluids flowing through the base and lid, respectively. In other configurations, a manifold may be provided to direct fluid from each source of fluid pressure to multiple devices 10. In some implementations, the fluid sources may include additives in addition to the fluids, such as salt or $CO_2$ as non-limiting examples.

Figure 10A:
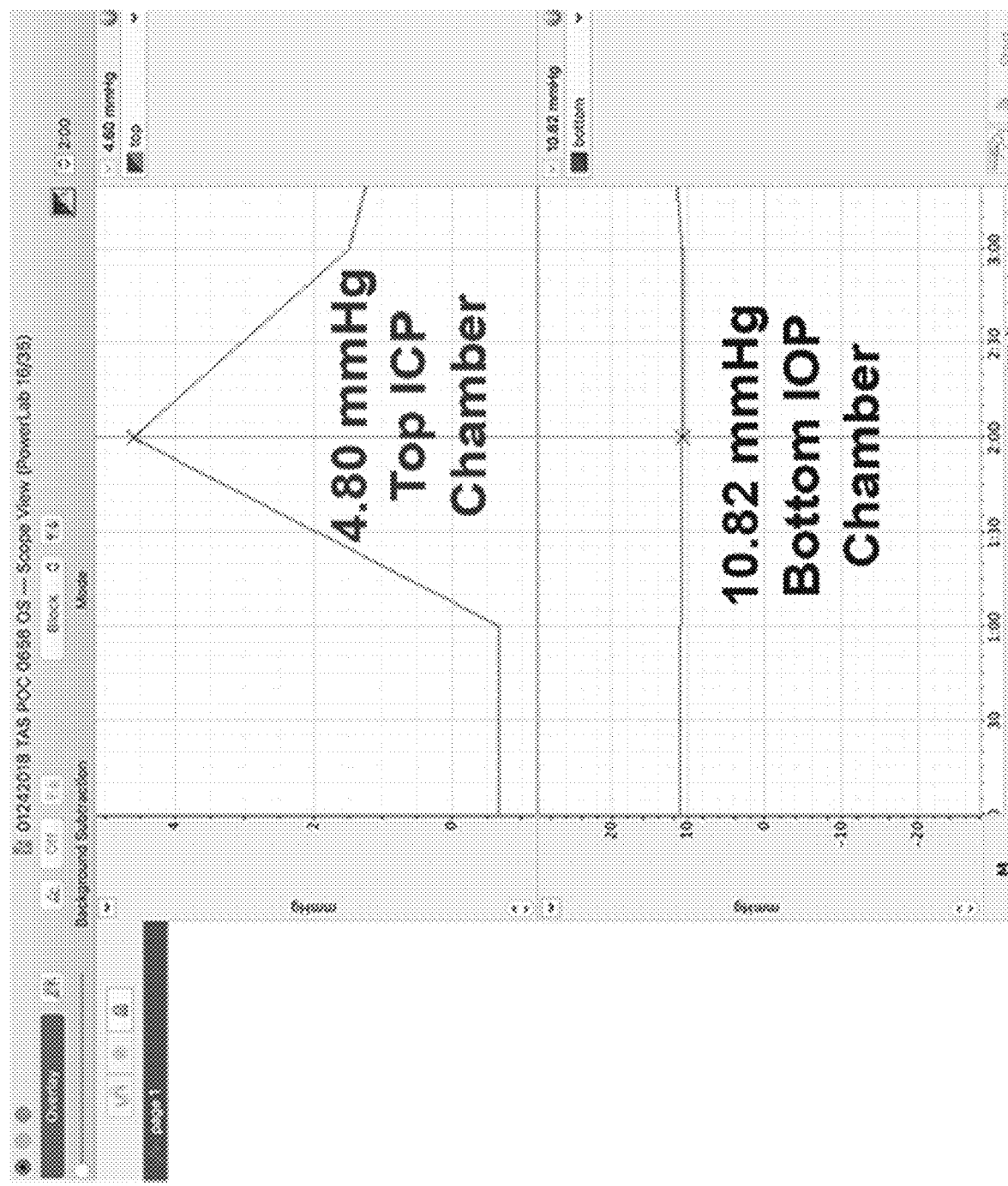
FIGS. 10A and 10B depict graphical representations of independent modulation of pressures in upper and lower chambers of one of the present devices.
Figure 10B:
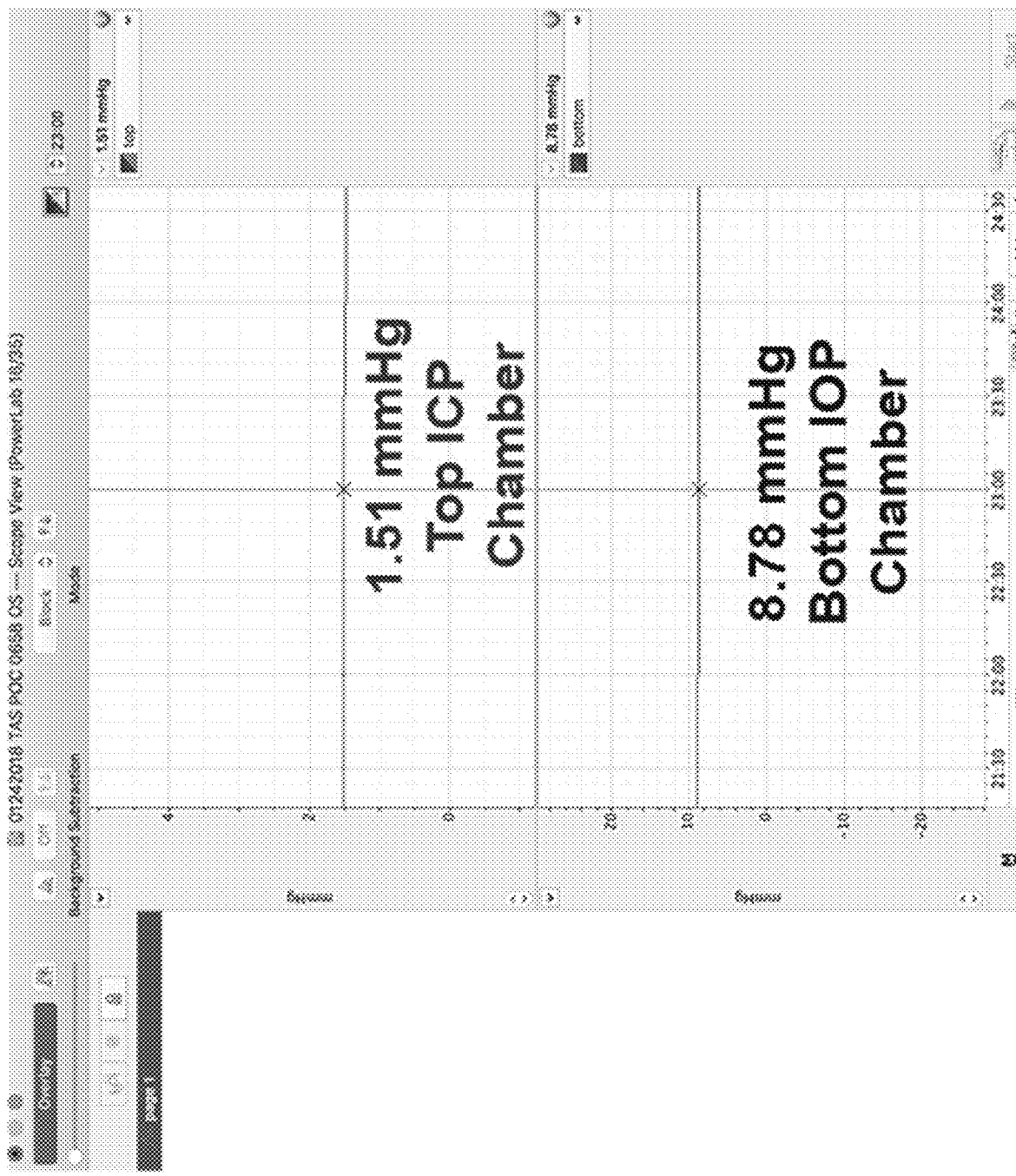

The present methods (for modeling ocular translaminar pressure gradients) can comprise, in one of the present devices or systems having a donor eye cup (e.g., 14) secured between retainer 22 and base 18, and lid 26 coupled to base 18: adjusting a fluid pressure gradient between a first fluid pressure in the one or more fluid ports (58) of the base and a second fluid pressure in the one or more fluid ports (106) of the lid, and thereby adjusting a corresponding fluid pressure gradient between the first fluid pressure on one side of the donor eye cup between the donor eye cup and the protrusion and the second fluid pressure on the other side of the donor eye cup in the chamber of the lid. Some such methods further comprise varying the fluid pressure gradient over time. For example, the simulated ICP in chamber 98 can be varied over time while the simulated IOP between the donor eye cup and protrusion 50 is held relatively constant, as charted in FIG. 10A, both can be held relatively constant as shown in FIG. 10B, or the simulated ICP can be held relatively constant while the simulated IOP is varied over time. The respective fluid pressures can be adjusted by adjusting the relative heights of fluid reservoirs respectively coupled to the fluid inlets of the base and lid. In other configurations, the pressure can be varied by adjusting respective perfusion pumps. In some implementations, the respective fluid pressures can be adjusted by a control device, as further described with reference to FIG. 18.

Some implementations of the present methods further comprise: measuring the first fluid pressure with a first pressure transducer coupled to a second one of fluid ports 58 of the base; and measuring the second fluid pressure with a second pressure transducer coupled to a second one of fluid ports 106 of the lid. For example, the pressure can be monitored with a personal computer (e.g., a PC running a Windows operating system) and a laboratory software program such as LabChart (e.g., LabChart Version 8).

Figure 11A:
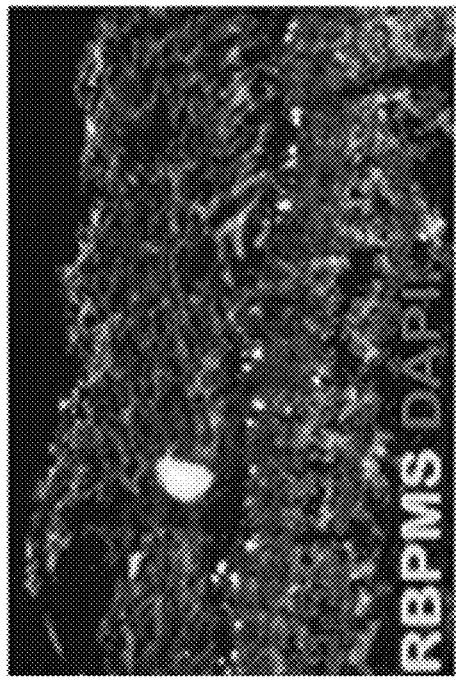
FIGS. 11A-11D depict representation images of retina and optical nerve head (ONH) sections from a human posterior eye cup after being cultured in one of the present devices for seven days.
Figure 11D:
Figure 11B:
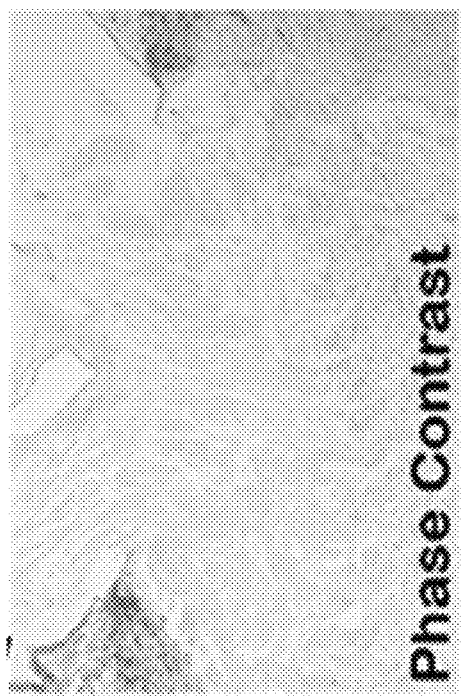
Figure 11C:
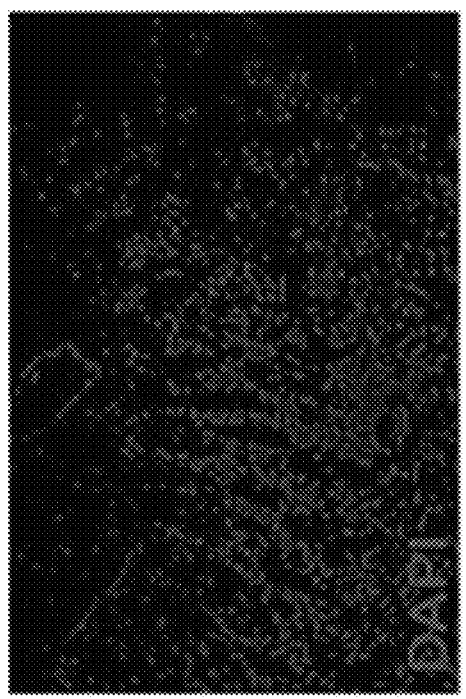

Some implementations of the present methods also include controlling the temperature of the device and donor eye cup. For example, in testing with the depicted prototypes, a donor human posterior eye cup was cultured for seven days with the device in an Heracell 150i incubator to maintain a temperature of 37° C. After this culture, the donor eye cup was removed from the device and portions of the retina and ONH were sectioned and imaged, revealing healthy cells. FIG. 11A shows a representative image of DAPI-stained ONH cells to identify Rbpms-positive cells, the presence of which indicated the presence of healthy cells at the conclusion of the 7-day culture period. FIG. 11B shows a representative phase-contrast image of ONH cells; FIG. 11B shows a representative image of the ONH cells of FIG. 11B with DAPI-staining; and FIG. 11C shows a representative image merging the images of FIGS. 11B and 11C. As with FIG. 11A, FIGS. 11B, 11C, and 11D also indicate the presence of healthy ONH cells at the conclusion of the 7-day culture period.

Thus, the devices described with reference to FIGS. 1-9C enable ex vivo modeling of and dynamically changing translaminar pressure gradients across a donor eye cup to model IOP and ICP painlessly and without the use of lumbar punctures. IOP and ICP may be measured at the same time in the same human donor eye. The human eye tissue may be kept healthy for long periods of time, enabling tests for long time periods (such as seven or more days). In some implementations, changing the IOP or ICP pressure is simplified by changing a height of source of fluid pressure 118 and/or source of fluid pressure 122. Additionally, device 10 (and other devices described herein) may be utilized for various IOP/ICP related pathogenesis. Thus, posterior segments of human eye cups can be cultured in device 10 (or other devices described herein) and translaminar pressure on the human eye cups can be studied. In addition, various other preclinical experiments may be performed using the device 10. For example, human posterior eye cups may have the host cells decellularized with donor stem cells from patients with various diseases including Papilledema, Intracranial hypertension, traumatic brain injury with damage to the ONH, and hemorrhagic stroke. These donor cells can be differentiated to retinal cells and seeded in a human donor to study precision medicine, which can result in identification of genetic (e.g., cardiovascular health, male vs. female, etc.), environmental, or pathogenic conditions causing these diseases. Additionally, or alternatively, differences between right posterior cups compared to left posterior cups can be studied in device 10. Additionally, or alternatively, other factors that could be contributing to vision impairment can be studied. For example, the medium in either of the chambers could be perfused with additional $CO_2$ concentrations and/or higher salt concentrations to study the results. Additionally, device 10 (and other devices described herein) is small enough to be transported into space or placed in zero-gravity chambers for short-term and long-term studies. Additionally, device 10 (and other devices described herein) enable effective testing of various therapies, such as AAV2 gene therapy. Additionally, the medium can be collected for biomarker expression to target future therapies. Additionally, the device 10 enables identification of pathways or molecules that can be treated with drugs or gene therapy and testing of these therapies in animal models of ICP before translation to human clinical trials.

Figure 12:
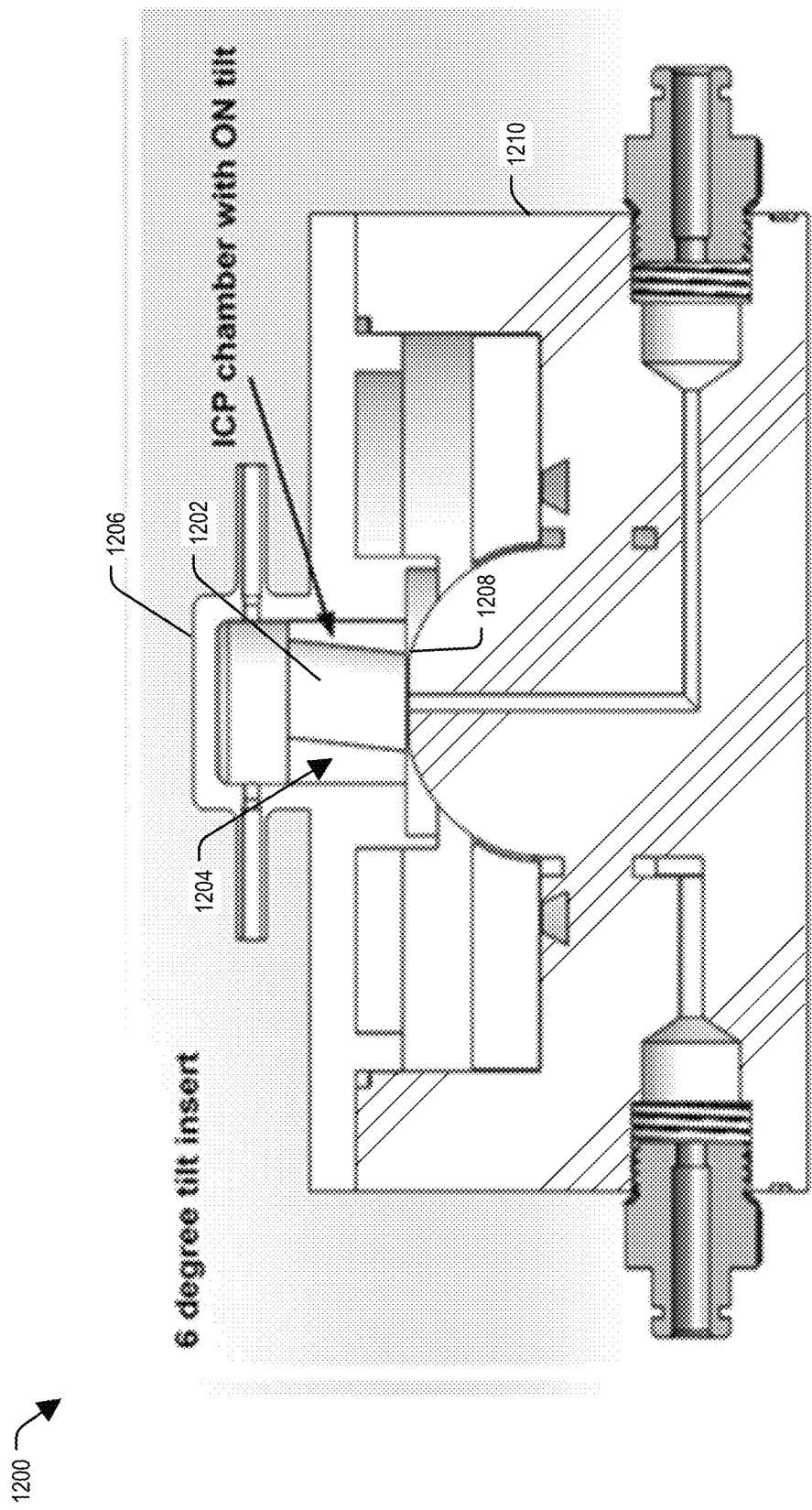
FIG. 12 depicts a cross-sectional view of a second implementation of one of the present devices that includes an insert that is a push to connect tubing in a chamber of a lid.
Figure 15C:
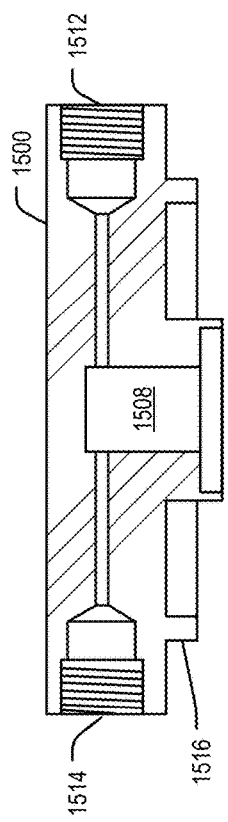
FIGS. 15A, 15B, 15C, 15D, and 15E depict top, side, first cross-sectional side, second cross-sectional side, and perspective views, respectively, of another example of a lid of one of the present devices.
Figure 15D:
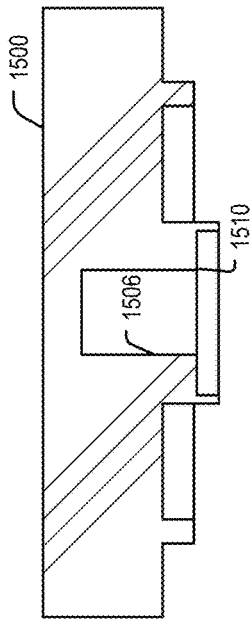
Figure 15E:
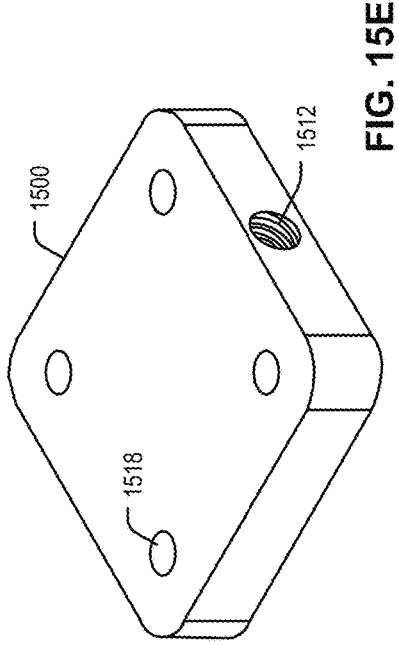
Figure 15A:
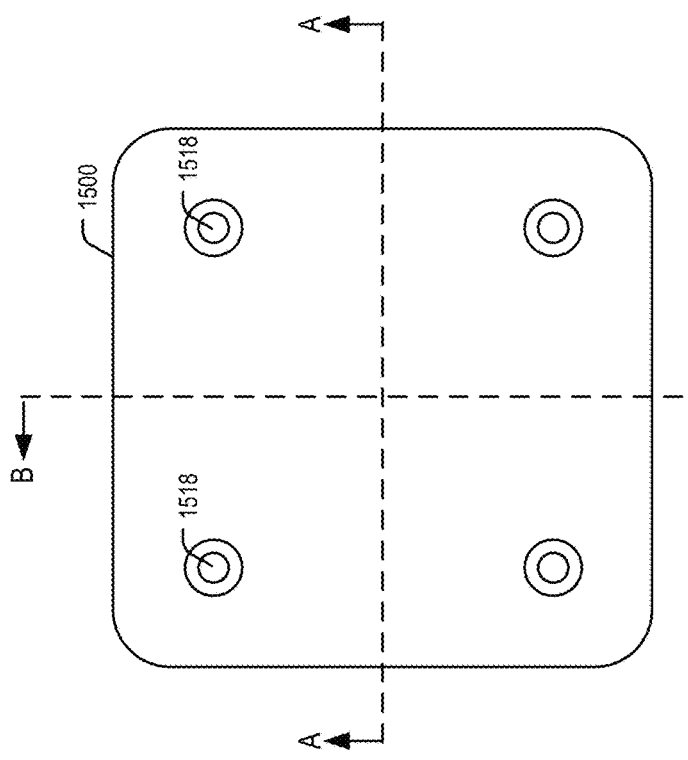
Figure 15B:
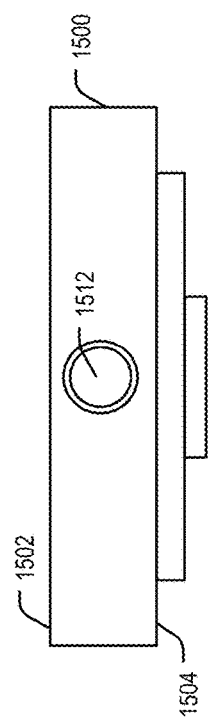

Referring to FIG. 12, a cross-sectional view of an example of a device 1200 for modeling translaminar pressure gradients is shown and designated 1200. Device 1200 may be similar to device 10, or to devices further described herein, except that device 1200 includes an insert 1202 in chamber 1204 of lid 1206. In a particular implementation, insert 1202 includes a push to connect tubing or tube fitting. Insert 1202 may be disposed at an angle from a vertical axis of protrusion 1208 of base 1210. In some implementations, insert 1202 is disposed at an angle between substantially 6° and substantially 10° from the axis. In a particular implementation, insert 1202 is disposed at substantially a 6° angle to the axis. In another particular implementation, insert 1202 is disposed at substantially a 10° angle to the axis. Insert 1202 is configured to move the optic nerve (based on the angle) to mimic the degree of head down tilt (HDT) experienced by astronauts during space flight.

Thus, device 1200 enables the study of translaminar pressure gradients on human posterior eye cups, similar to device 10, and also enables the study of HDT through the movement of the optic nerve by insert 1202. Device 1200 may also enable study of Spaceflight-Associated Neuro-Ocular Syndrome (SANS). For example, the ex vivo model of the human posterior cup can be used for classification of cellular and functional modifications that occur due to chronic mild elevation of ICP under conditions of microgravity. To illustrate, device 1200 may be placed in a zero gravity chamber or taken on space flight to enable testing in various conditions. Additionally, the model can be used to test countermeasures like artificial gravity and to identify therapies and treatments that can directly save RGCs from neurodegeneration as observed in SANS.

Referring to FIGS. 13A-13D, top, side, first cross-sectional side (along line AA), and second cross section side (along line BB) views, respectively, of a base 1300 are shown. Base 1300 may be part of an ocular translaminar pressure gradient modeling device (similar to device 10) that also includes the retainer ring FIGS. 14A-14C and the lid of FIGS. 15A-15E. In such a device, tubing (e.g., conduits) and sources of fluid pressure (e.g., syringes or fluid reservoirs) are similarly included, as described with reference to FIGS. 1, 2, 3A-3B, 4A-4B, 5A-5C, and 6A-6C.

As shown in FIGS. 13A-13D, base 1300 has a first end 1302 and a second end 1304 and defines a recess 1306 extending from first end 1302 to a bottom 1308 defined between the first and second ends. Base 1300 also defines a protrusion 1310 extending upward from bottom 1308 to an upper end 1312 disposed between bottom 1308 and first end 1302. Upper end 1312 of the protrusion is sized to receive a donor eye cup over the upper end. For example, in the depicted implementation, protrusion 1310 has a circular cross-section, upper end 1312 (and an entirety of protrusion 1310) is hemispherical, and each of protrusion 1310 and upper end 1312 has a diameter about equal to or slightly smaller than an average diameter of a donor eye cup. In the depicted configuration, recess 1306 has a circular cross-sectional shape which, together with protrusion 1310, defines an annular space around the protrusion, which annular space is sized to receive a retainer ring of FIGS. 14A-14C to secure the donor eye cup. In a particular implementation, base 1300 is substantially square-shaped and recess 1306 has a circular cross-sectional shape.

Base 1300 also defines a first fluid port 1314 extending through the upper end of the protrusion to enable fluid pressure to be communicated to the space between the donor eye cup and the upper end to simulate IOP. Base 1300 also defines a second fluid port 1316 that extends below protrusion 1310 and is configured to enable a pressure sensor to measure the pressure between the donor eye cup and upper end 1312 (e.g., the simulated IOP). In the depicted implementation, second fluid port 1316 does not extend through upper end 1312. In some implementations, at least portions of fluid ports 1314, 1316 are threaded, as illustrated in FIG. 13D.

In the implementation shown, base 1300 also defines a plurality of retainer holes 1320 and a plurality of lid holes 1322, for securing a retainer ring and a lid, respectively, to base 1300. The plurality of retainer holes 1320 and the plurality of lid holes 1322 may be threaded. In other implementations, the base, retainer ring, and lid may be configured to be secured to one another in any suitable way and/or with any suitable structure.

Additionally, in the depicted configuration, base 1300 defines a groove or notch 1330 around the upper perimeter of recess 1306, which groove or notch 1330 is configured to receive an O-ring or seal to assist with sealing the interface between the lid and base 1300 when the lid is coupled to the base. Base 1300 also defines grooves 1332 configured to receive an O-ring or seal to assist with sealing the interface between base 1300 and the retainer ring.

FIG. 13E depicts an expanded view of portion 1340 of FIG. 13C. In the expanded view, a detailed view of groove 1332 (e.g., O-ring groove) is shown.

Referring to FIGS. 14A-14C, top, cross-sectional side, and side views, respectively, of a retainer ring 1400 are shown. Retainer ring 1400 is configured to fit around and over protrusion 1310 and to be coupled to base 1300 to secure the donor eye cup between the retainer and the base and to seal the interface between the donor eye cup and the protrusion. For example, retainer ring 1400 may be provided with an annular shape defining a central opening 1402 having a diameter that is about equal to or slightly larger than the outer diameter of protrusion 1310 at the point at which retainer ring 1400 is secured to base 1300. By way of example, in some embodiments, the difference in these diameters may be such that a space between the protrusion and the portion of retainer ring 1400 that is closest to protrusion 1310 is smaller than an average thickness of a corresponding portion of a wall of a donor eye cup (and/or smaller than the thickness of the corresponding portion of the wall of an actual donor eye cup) with which the device is intended to function. In the depicted implementation, retainer ring 1400 also defines a plurality of holes 1404 configured to be aligned with retainer holes 1320 in base 1300 such that the retainer can be secured to the base with screws or bolts. An interior wall 1406 defining the central opening is angled so that the central opening is larger at the bottom than at the top. This angle, and the resulting narrower top of the central opening, assists with securing the donor eye cup by pinching the donor eye cup wall between retainer ring 1400 and protrusion 1310 of base 1300.

Referring to FIGS. 15A-15E, top, side, first cross-sectional side (along line AA), second cross-sectional side (along line BB), and perspective views, respectively, of a lid 1500 are shown. Lid 1500 has a first side 1502, a second side 1504 configured to face base 1300, and an annular sidewall 1506 on the second side. As shown, annular sidewall 1506 defines a chamber 1508 and has a distal end 1510 that encircles an open end of the chamber. Distal end 1510 of annular sidewall 1506 is configured such that when lid 1500 is secured relative to base 1300 and a donor eye cup is secured to protrusion 1310, distal end 1510 extends into recess 1306 of the base to secure the donor eye cup between annular sidewall 1506 and protrusion 1310 and to seal the interface between annular sidewall 1506 and the donor eye cup. This seal can be provided any of various ways. For example, in the implementations shown, the inner diameter of annular sidewall 1506 at distal end 1510 is smaller than the maximum outer diameter of protrusion 1310, and distal end 1510 extends only part way down the hemispherical upper end of protrusion 1310 to a point at which a minimum distance between upper end 1312 of protrusion 1310 and distal end 1510 of annular sidewall 1506 of lid 1500 is smaller than an average thickness of a wall of a donor eye cup (and/or an actual thickness of a corresponding portion of a donor eye cup) with which the device is intended to be used. As a result, protrusion 1310 and distal end 1510 pinch the donor eye cup and chamber 1508 can be pressurized to simulate ICP on the outer side of the donor eye cup (with the ONH). Lid 1500 also defines a first fluid port 1512 and a second fluid port 1514 in fluid communication with chamber 1508. First fluid port 1512 may be configured to be coupled (via a conduit) to a fluid pressure source and second fluid port 1514 may be configured to be coupled (via a conduit) to a pressure sensor (e.g., a pressure transducer).

In the implementation shown, lid 1500 also defines an outer annular sidewall 1516 on second side 1504, which sidewall 1516 has an outer diameter about equal to or just smaller than the inner wall of base 1300 defining recess 1306. The outer surface of outer annular sidewall 1516 therefore cooperates with notch or groove 1330 of base 1300 to compress an O-ring or seal in that notch or groove to help seal the interface between the lid and the base. In the depicted configuration, lid 1500 also defines a plurality of holes 1518 configured to be aligned with lid holes 1322 in base 1300 such that the lid can be secured to the base with screws or bolts.

Figure 16A:
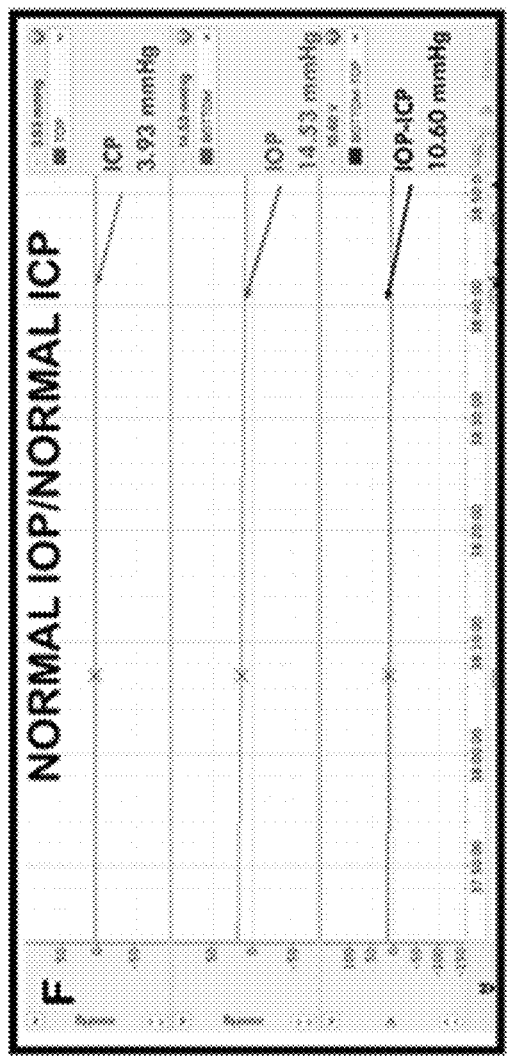
FIGS. 16A and 16B depict graphical representations of modulations of pressures in upper and lower chambers of one of the present devices.
Figure 16B:
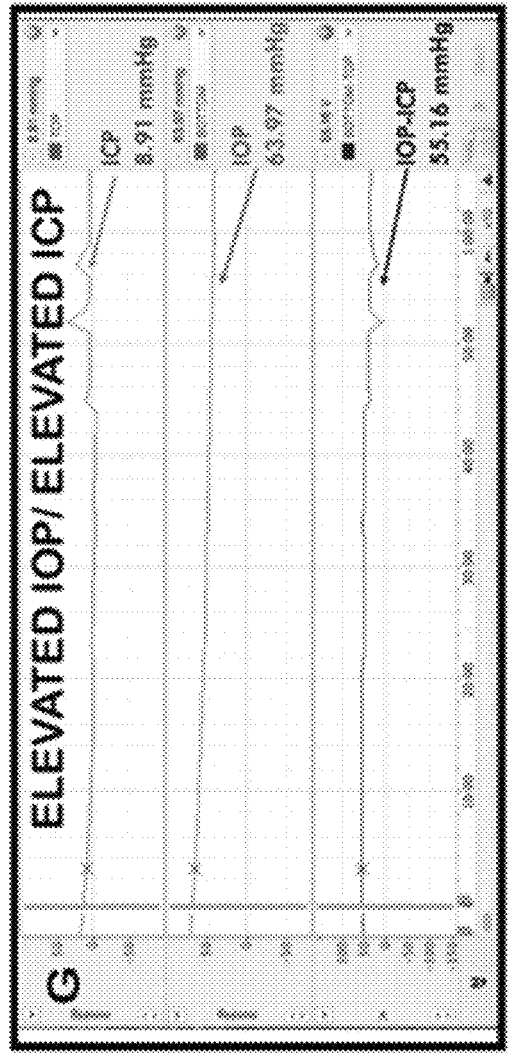

Referring to FIGS. 16A-16B, graphical representations of modulations of pressures in upper and lower chambers of one of the present devices are shown. For example, the simulated ICP in a chamber (e.g., chamber 98 or chamber 1508) can be held relatively constant and at "normal" levels while the simulated IOP between the donor eye cup and a protrusion (e.g., protrusion 50 or protrusion 1310) can be held relatively constant and at "normal" levels, as charted in FIG. 16A. Alternatively, the simulated ICP and the simulated IOP may be modulated and maintained at "elevated" levels as charted in FIG. 16B.

Figure 17A:
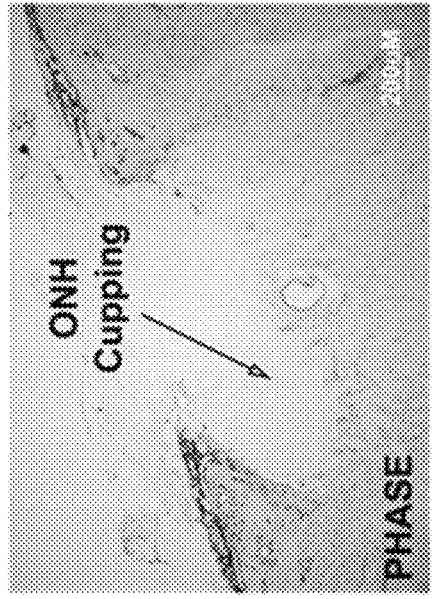
FIGS. 17A, 17B, 17C, and 17D depict graphical representations of retina and ONH of a human posterior eye cup after being cultured in one of the present devices.
Figure 17B:
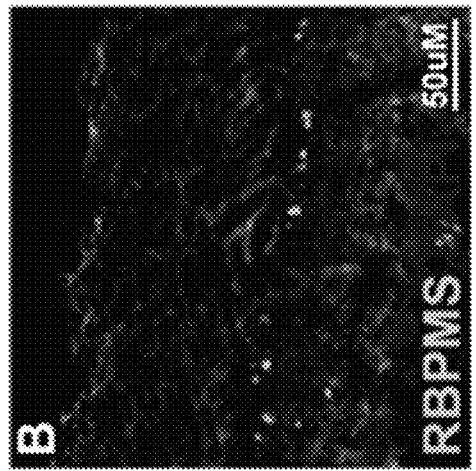
Figure 17C:
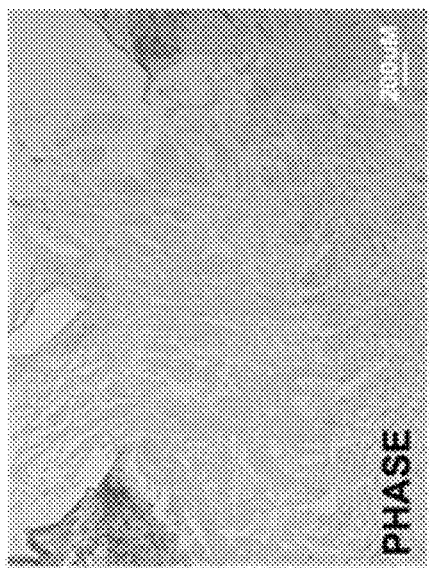
Figure 17D:
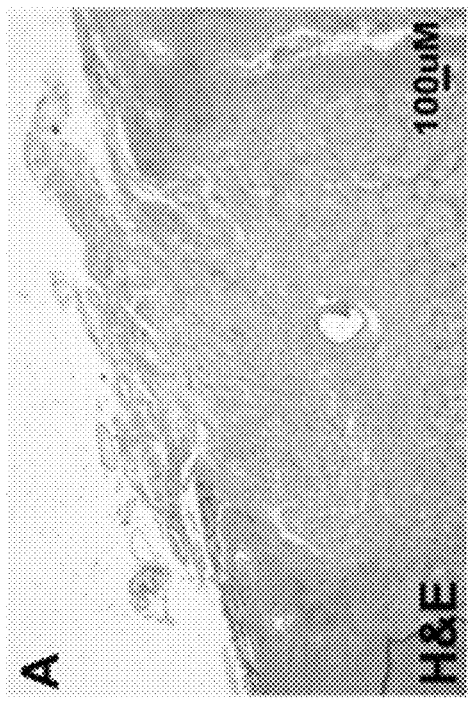

Referring to FIGS. 17A-17D, graphical representations of retina and ONH of a human posterior eye cup after being cultured in one of the present devices are shown. In a particular implementation, the human posterior eye cup was cultured for seven days in one of the devices (e.g., device 10, prototype 10a, prototype 10b, device 1200, or a device that includes base 1300, retainer ring 1400, and lid 1500). After the culture, the donor eye cup was removed from the device and portions of the retina and ONH were sectioned and imaged. FIG. 17A shows a representative phase-contrast image of the retina and the ONH under "normal" ICP. FIG. 17B shows a representative phase-contrast image of the retina and the ONH under "elevated" translaminar pressure gradient (TLPG), for example greater than 15 mmHg. As can be seen in FIG. 17B, the ONH exhibits cupping under the elevated TLPG. A Hematoxylin and eosin stain was performed on a cross-section of the ONH under stimulation of the elevated TLPG, as shown in FIG. 17C. FIG. 17D shows a representative image of DAPI-stained ONH cells to identify Rbpms-positive cells, the presence of which indicated the presence of healthy cells at the conclusion of the seven day culture period. As shown in FIG. 17C, the ONH exhibited cupping and, as illustrated in FIG. 17D, the number of RGCs were decreased.

Figure 18:
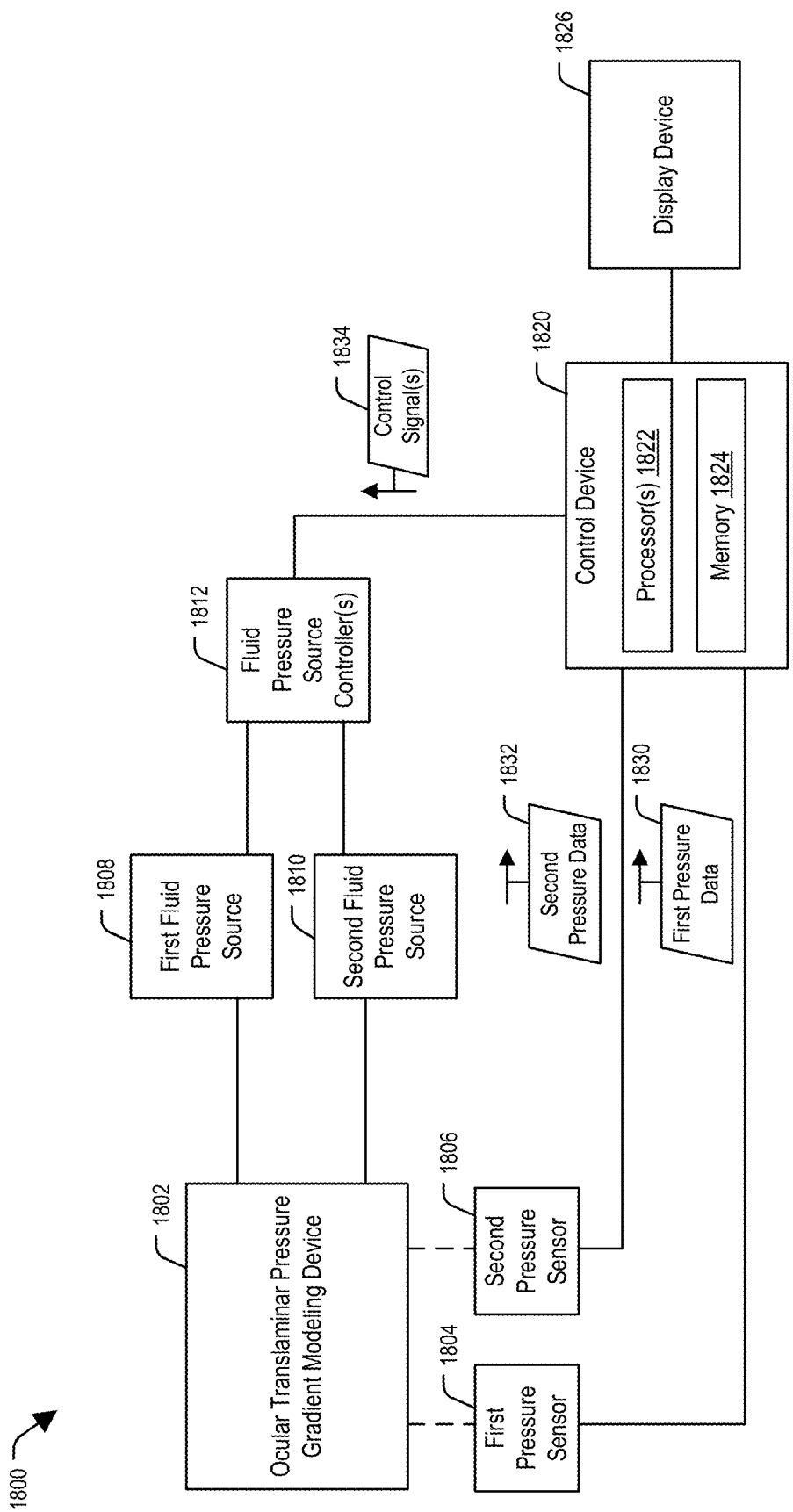
FIG. 18 depicts a block diagram of an example of a system for modeling ocular translaminar pressure gradients.

Referring to FIG. 18, a system for modeling ocular translaminar pressure gradients is shown and designated 1800. System 1800 includes an ocular translaminar pressure gradient modeling device 1802, a first pressure sensor 1804, a second pressure sensor 1806, a first fluid pressure source 1808, a second fluid pressure source 1810, one or more fluid pressure source controllers 1812, a control device 1820, and a display device 1826. In a particular implementation, ocular translaminar pressure gradient modeling device 1802 includes or corresponds to device 10, prototype 10a, prototype 10b, device 1200, or a device that includes base 1300, retainer ring 1400, and lid 1500. Ocular translaminar pressure gradient modeling device 1802 is configured to receive a donor eye cup on a protrusion of a base of ocular translaminar pressure gradient modeling device 1802.

First fluid pressure source 1808 is coupled by a first conduit to a first fluid port extending through the protrusion of the base of ocular translaminar pressure gradient modeling device 1802. First fluid pressure source 1808 is in fluid communication with the first fluid port and is configured to provide fluid pressure by providing a first fluid to the base of ocular translaminar pressure gradient modeling device 1802. Second fluid pressure source 1810 is coupled by a second conduit to a second fluid port defined in a lid of ocular translaminar pressure gradient modeling device 1802. Second fluid pressure source 1810 is in fluid communication with the second fluid port and is configured to provide fluid pressure by providing a second fluid to a chamber within the lid of ocular translaminar pressure gradient modeling device 1802. Fluid pressure provided by first fluid pressure source 1808 may simulate IOP and fluid pressure provided by second fluid pressure source 1810 may simulate IOP.

In a particular implementation, first fluid pressure source 1808 and second fluid pressure source 1810 include syringes. In this implementation, fluid pressure provided by fluid pressure sources 1808, 1810 is based on a height (e.g., a distance above the ocular translaminar pressure gradient modeling device 1802) of the corresponding fluid pressure source. In an alternate implementation, first fluid pressure source 1808 and second fluid pressure source 1810 include pumps, such as perfusion pumps. In this implementation, the fluid pressure provided by fluid pressure sources 1808, 1810 is controlled by a pump controller.

In some implementations, fluid pressure sources 1808, 1810 may include additives in addition to fluids. For example, the fluids may be water, saline, or another sterilized fluid, and the fluids may include one or more additional additives. As a first example, the fluids may include salt to increase the salt concentration of the fluids. As another example, the fluids may include $CO_2$ to increase the $CO_2$ concentration within the fluids. Other additives are also possible.

First fluid pressure source 1808 and second fluid pressure source 1810 are coupled to fluid pressure source controller 1812. Fluid pressure source controller 1812 includes one or more controllers configured to control the amount of fluid pressure provided by the fluid pressure sources. In a particular implementation, the fluid pressure sources are syringes or reservoirs of fluid, and the amount of fluid pressure provided is based on the height of the respective fluid pressure source. In such implementations, fluid pressure sources 1808, 1810 may be coupled to one or more pulleys, one or more conveyor belts, or another motorized component that adjusts the height of the fluid pressure sources. In such implementations, fluid pressure source controller 1812 may include or correspond to the motors that operate the pulleys, conveyor belts, or other components. In an alternate implementation, fluid pressure sources 1808, 1810 include pumps, and fluid pressure source controller 1812 includes the controllers of the respective pumps. In such implementations, fluid pressure source controller 1812 may adjust parameters of the pumps to control the amount of fluid pressure provided by the pumps.

First pressure sensor 1804 and second pressure sensor 1806 are coupled to ocular translaminar pressure gradient modeling device 1802 and configured to measure fluid pressures within ocular translaminar pressure gradient modeling device 1802. For example, first pressure sensor 1804 is coupled by a third conduit to a third fluid port in the base of ocular translaminar pressure gradient modeling device 1802 and is configured to measure a pressure beneath the donor eye cup (e.g., a pressure simulating IOP). In a particular implementation, the third fluid port extends through the protrusion in the base of the ocular translaminar pressure gradient modeling device 1802, as illustrated in FIG. 5C. In an alternate implementation, the third fluid port extends only partially below the protrusion, as illustrated in FIG. 13D. Second pressure sensor 1806 is coupled by a fourth conduit to a fourth fluid port in the lid of ocular translaminar pressure gradient modeling device 1802 and is configured to measure a pressure in the chamber above the donor eye cup (e.g., a pressure simulating ICP). In a particular implementation, first pressure sensor 1804 and second pressure sensor 1806 are pressure transducers. First pressure sensor 1804 and second pressure sensor 1806 are configured to generate and send corresponding pressure data to control device 1820.

Control device 1820 is configured to perform control operations for system 1800. Control device 1820 includes one or more processors 1822 and at least one memory 1824 coupled to the one or more processors 1822 (e.g., via a bus). Memory 1824 may include read only memory (ROM) devices (e.g., programmable read-only memory (PROM), erasable programmable read-only memory (EPROM), electrically erasable programmable read-only memory (EEPROM), optical storage, or the like), random-access memory (RAM) devices (e.g., synchronous RAM (SRAM), dynamic RAM (DRAM), synchronous dynamic RAM (SDRAM), or the like), one or more HDDs, flash memory devices, SSDs, other devices configured to store data in a persistent or non-persistent state, or a combination of different memory devices. Memory 1824 may store instructions that, when executed by one or more processors 1822, cause one or more processors 1822 to perform the operations described herein. Although described as including one or more processors 1822, in other implementations, control device 1820 can include application specific integrated circuits (ASIC), field-programmable gate arrays (FPGA), very large scale integrated (VLSI) circuits, or other circuitry. Additionally, control device 1820 may include an interface, such as a wired interface or a wireless interface, to enable communication with one or more components of system 1800. Control device 1820 may also include a user interface to enable a user to control operations of system 1800.

Display device 1826 is coupled to control device 1820 and configured to display data received from control device 1820, such as pressure data, image data, etc. The data may be displayed in a graphical user interface (GUI). In a particular implementation, display device 1826 is external to control device 1820. In other implementations, display device 1826 may be included or integrated within control device 1820.

During operation, control device 1820 may receive a user input indicating a first parameter of first fluid pressure source 1808 and a second parameter of second fluid pressure source 1810. The aspects may be heights of the fluid pressure sources 1808, 1810 or target fluid pressures to be output by the fluid pressure sources 1808, 1810. In some implementations, the control device 1820 may be configured to determine a height that corresponds to a target fluid pressure.

Control device 1820 may generate and transmit control signals 1834 to fluid pressure source controller 1812 to control the fluid pressure sources 1808, 1810 to achieve the target parameters. For example, in implementations in which fluid pressure sources 1808, 1810 are syringes or reservoirs located above ocular translaminar pressure gradient modeling device 1802, control signals 1834 may correspond to voltages that are provided to motors to adjust the relative heights of fluid pressure sources 1808, 1810. In implementations in which fluid pressure sources 1808, 1810 are perfusion pumps, control signals 1834 may indicate an amount of fluid pressure to be output by each of the perfusion pumps.

As fluid pressure is provided to ocular translaminar pressure gradient modeling device 1802 by fluid pressure sources 1808, 1810, pressure sensors 1804, 1806 may measure pressures within ocular translaminar pressure gradient modeling device 1802. For example, first pressure sensor 1804 may measure the pressure below the donor eye cup (e.g., the simulated IOP) and generate and transmit first pressure data 1830 to control device 1820. Second pressure sensor 1806 may measure the pressure above the donor eye cup (e.g., the simulated ICP) and generate and transmit second pressure data 1832 to control device 1820.

Control device 1820 may receive the pressure data and use the pressure data to determine the translaminar pressure gradient experienced by the donor eye cup. For example, control device 1820 may compare the simulated IOP indicated by first pressure data 1830 to the simulated ICP indicated by second pressure data 1832 to determine the translaminar pressure gradient. Control device 1820 may also operate one or more sensors or other components to measure the effects of the translaminar pressure gradient on the donor eye cup. For example, in some implementations, ocular translaminar pressure gradient modeling device 1802 may include a camera (or other sensor) in the chamber of the lid, and the control device 1820 may receive image data of images of the donor eye cup during the experiment. Additionally, control device 1820 may provide data to display device 1826 for display to a user. For example, display device 1826 may display pressure measurements, translaminar pressure gradients, images of the donor eye cup, or a combination thereof, to enable study of the effects of the translaminar pressure gradient on the donor eye cup.

Figure 19:
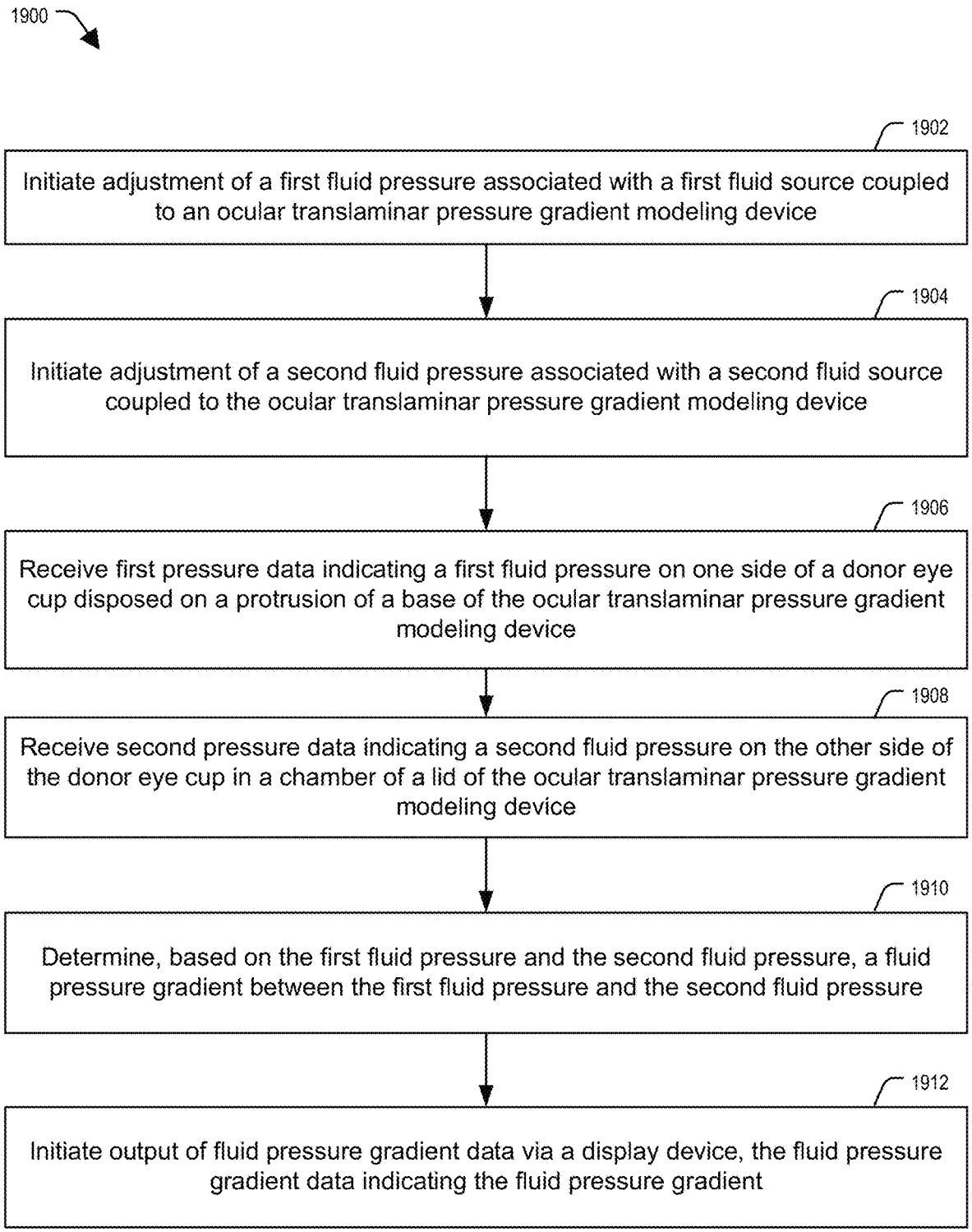
FIG. 19 depicts a flow chart of an example of a method of modeling an ocular translaminar pressure gradient.

FIG. 19, is a flow diagram of a method 1900 of modeling an ocular translaminar pressure gradient. Method 1900 may be stored in a computer-readable storage medium as instructions that, when executed by one or more processors, cause the one or more processors to perform the operations of the method 1900. In a particular implementation, method 1900 may be performed by control device 1820 using device 10, prototype 10a, prototype 10b, device 1200, or a device that includes base 1300, retainer ring 1400, and lid 1500.

At 1902, method 1900 includes initiating adjustment of a first fluid pressure associated with a first fluid source coupled to an ocular translaminar pressure gradient modeling device. For example, control device 1820 may transmit control signals 1834 to fluid pressure source controller 1812 to control a parameter of first fluid pressure source 1808, such as a relative height or a pump pressure.

At 1904, method 1900 includes initiating adjustment of a second fluid pressure associated with a second fluid source coupled to the ocular translaminar pressure gradient modeling device. For example, control device 1820 may transmit control signals 1834 to fluid pressure source controller 1812 to control a parameter of second fluid pressure source 1810, such as a relative height or a pump pressure.

At 1906, method 1900 includes receiving first pressure data indicating a first fluid pressure on one side of a donor eye cup disposed on a protrusion of a base of the ocular translaminar pressure gradient modeling device. For example, control device 1820 may receive first pressure data 1830 from first pressure sensor 1804. First pressure data 1830 may indicate a pressure on one side of a donor eye cup disposed on protrusion 50 or protrusion 1310 (e.g., the simulated IOP).

At 1908, method 1900 includes receiving second pressure data indicating a second fluid pressure on the other side of the donor eye cup in a chamber of a lid of the ocular translaminar pressure gradient modeling device. For example, control device 1820 may receive second pressure data 1832 from second pressure sensor 1806. Second pressure data 1832 may indicate a pressure on the other side of the donor eye cup in chamber 98 or chamber 1508 (e.g., the simulated ICP).

At 1910, method 1900 includes determining, based on the first fluid pressure and the second fluid pressure, a fluid pressure gradient between the first fluid pressure and the second fluid pressure. For example, control device 1820 may compare the fluid pressure indicated by first pressure data 1830 to the fluid pressure indicated by second pressure data 1832 to determine the translaminar pressure gradient.

At 1912, method 1900 further includes initiating output of fluid pressure gradient data via a display device, the fluid pressure gradient data indicating the fluid pressure gradient. For example, the translaminar pressure gradient may be displayed via display device 1826.

In a particular implementation, method 1900 further includes causing one or more sensors to measure the donor eye cup within the ocular translaminar pressure gradient modeling device. For example, control device 1820 may cause a camera in chamber 98 or chamber 1508 to take images of the donor eye cup and provide image data to control device 1820 for display via display device 1826.

Thus, method 1900 enables modeling of ocular translaminar pressure gradients. Such modeling may be used to study the effects of the ocular translaminar pressure gradient on the optic nerve, which may result in treatment for various eye diseases.

Referring to FIGS. 20A-20D, 21A-21C, and 22A-22F, another example of a base, retainer ring, and lid according to the present disclosure are shown. FIGS. 20A-20D, 21A-21C, and 22A-22F depict a particular illustrative implementation having various dimensions. Such dimensions are not intended to be limiting, and in other examples, the dimensions shown in FIGS. 20A-20D, 21A-21C, and 22A-22F may have other values. In a device formed by the base, the retainer ring, and the lid, tubing (e.g., conduits) and sources of fluid pressure (e.g., syringes or fluid reservoirs) are similarly included, as described with reference to FIGS. 1, 2, 3A-3B, 4A-4B, 5A-5C, and 6A-6C.

Figure 20C:
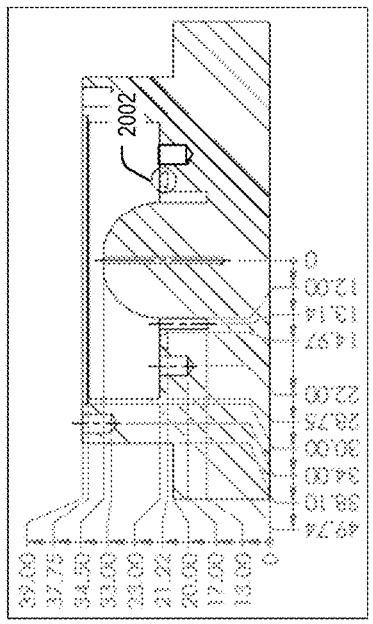
FIGS. 20A, 20B, 20C, and 20D depict top, side, first cross-sectional side, and second cross-section side views, respectively, of another example of a base of one of the present devices.
Figure 20D:
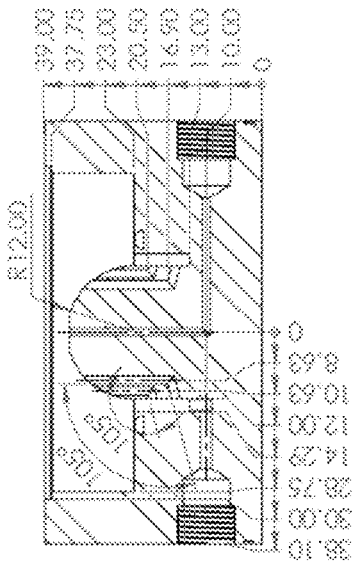
Figure 20E:
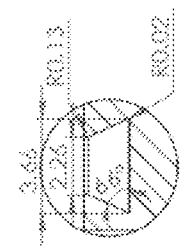
FIG. 20E depicts an expended view of a portion of FIG. 20C.
Figure 20A:
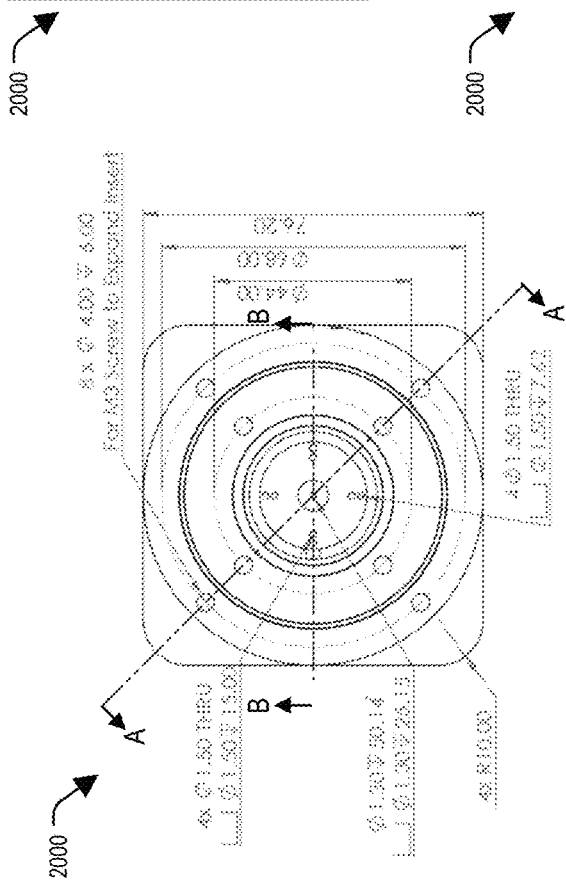
Figure 20B:
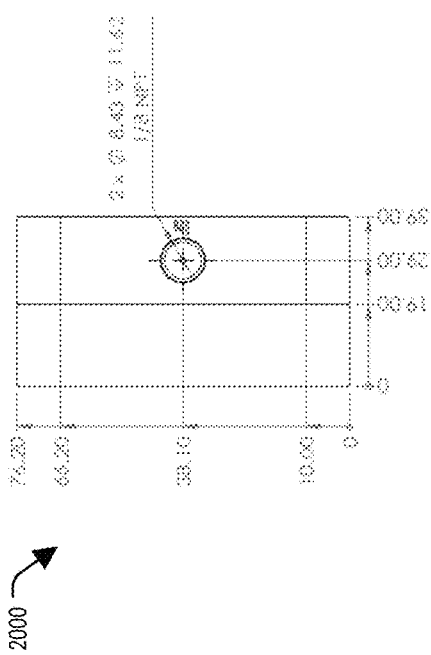

FIGS. 20A-20E depict base 2000. In a particular implementation, base 2000 includes or corresponds to base 1300 of FIGS. 13A-13E. FIG. 20A depicts a top view of a base 2000. FIG. 20B depicts a side view of base 2000. FIG. 20C depicts a first cross-sectional side view of base 2000 along line BB. FIG. 20D depicts a second cross-sectional side view of base 2000 along line AA. FIG. 20E depicts an expanded view of portion 2002 of FIG. 20C including an O-ring groove.

Figures 21A, 21B, 21C:
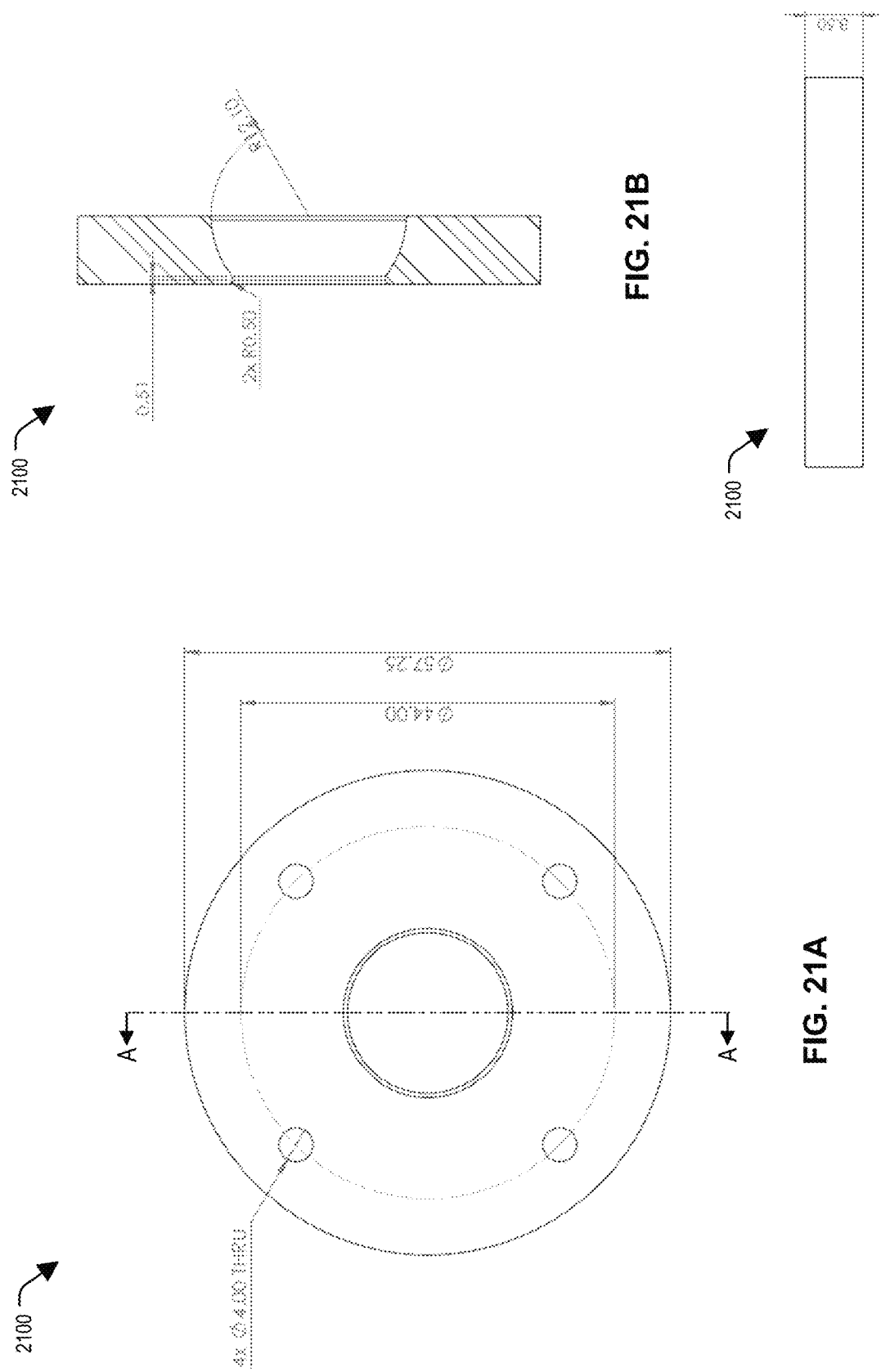
FIGS. 21A, 21B, and 21C depict top, cross-sectional side, and side views, respectively, of another example of a retainer ring of one of the present devices.

FIGS. 21A-21C depict retainer ring 2100, which may be used with base 2000 as part of an ocular translaminar pressure gradient modeling device. In a particular implementation, retainer ring 2100 includes or corresponds to retainer ring 1400 of FIGS. 14A-14C. FIG. 21A depicts a top view of retainer ring 2100. FIG. 21B depicts a cross-sectional side view of retainer ring 2100 along line AA. FIG. 21C depicts a side view of retainer ring 2100.

Figure 22E:
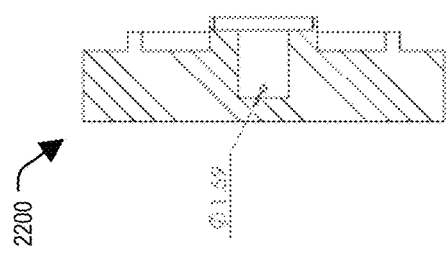
FIGS. 22A, 22B, 22C, 22D, 22E, and 22F depict top, first side, first cross-sectional side, second side, second cross-sectional side, and perspective views, respectively, of another example of a lid of one of the present devices.
Figure 22D:
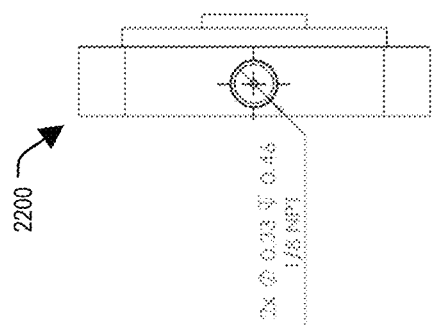
Figure 22F:
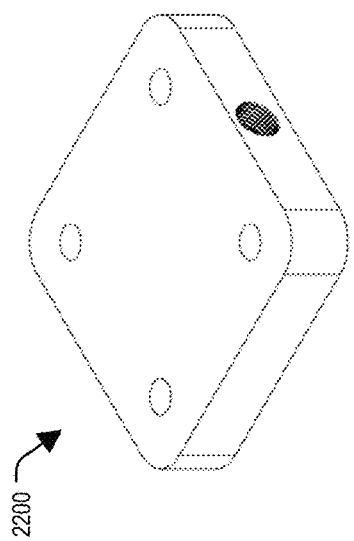
Figure 22A:
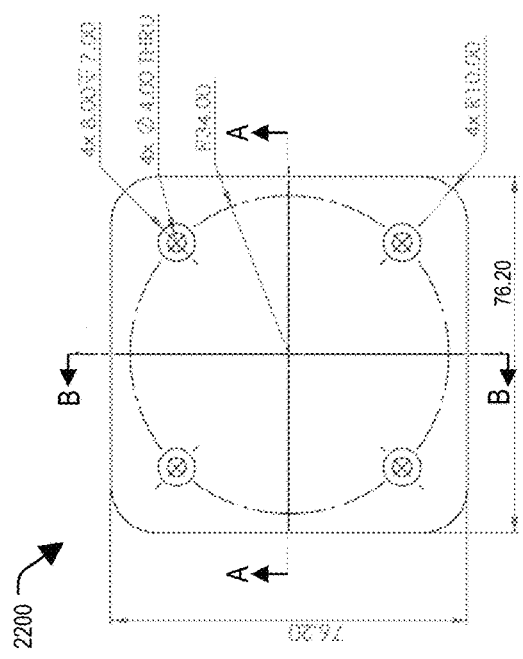
Figure 22B:
Figure 22C:
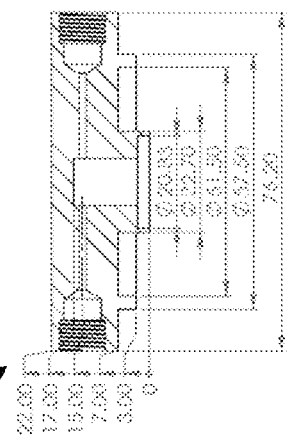

FIGS. 22A-22F depict lid 2200, which may be used with base 2000 and retainer ring 2100 as part of an ocular translaminar pressure gradient modeling device. In a particular implementation, lid 2200 includes or corresponds to lid 1500 of FIGS. 15A-15E. FIG. 22A depicts a top view of lid 2200. FIG. 22B depicts a first side view of lid 2200. FIG. 22C depicts a first cross-sectional side view of lid 2200 along line AA. FIG. 22D depicts a second side view of lid 2200. FIG. 22E depicts a second cross-sectional side view of lid 2200 along line BB. FIG. 22F depicts a perspective view of lid 2200.

Figure 23A:
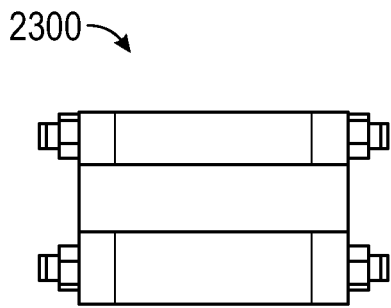
FIGS. 23A, 23B, 23C, 23D, 23E, and 23F depict front, left, top, perspective, transparent, and perspective views, respectively, of another example of one of the present devices.
Figure 23D:
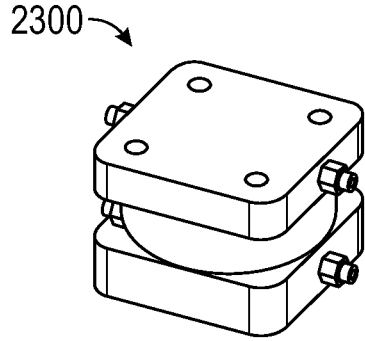
Figure 23B:
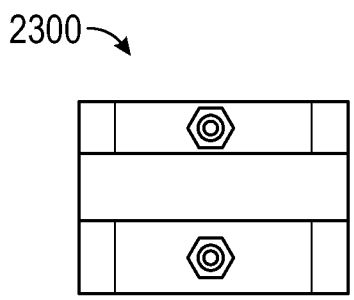
Figure 23E:
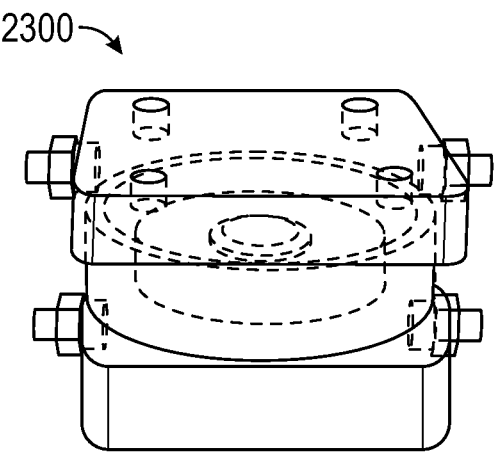
Figure 23C:
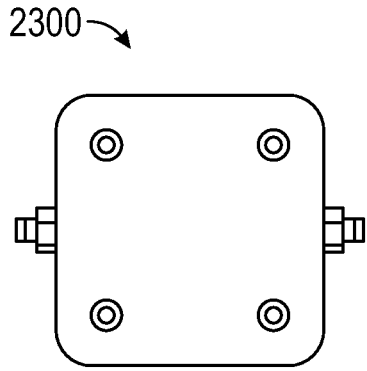
Figure 23F:
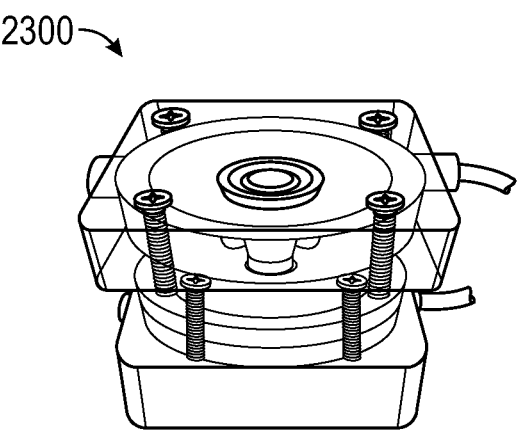

Referring to FIGS. 23A-23F, views of a device 2300 are shown. The device 2300 may include or correspond to an ocular translaminar pressure gradient modeling device that includes base 1300 of FIGS. 13A-13E, retainer ring 1400 of FIGS. 14A-14C, and lid 1500 of FIGS. 15A-15E and/or by base 2000 of FIGS. 20A-20E, retainer ring 2100 of FIGS. 21A-21C, and lid 2200 of FIGS. 22A-22F. FIG. 23A depicts a front view of device 2300. FIG. 23B depicts a left view of device 2300. FIG. 23C depicts a top view of device 2300. FIG. 23D depicts a perspective view of device 2300. FIG. 23E depicts a transparent view of device 2300. FIG. 23F depicts a picture of a prototype of device 2300.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

REFERENCES

[1] Morgan W H, Yu D Y, Cooper R L, Alder V A, Cringle S J, Constable U, *The influence of cerebrospinal fluid pressure on the lamina cribrosa tissue pressure gradient*. Invest Ophthalmol Vis Sci. 1995 May; 36(6):1163-72.

[2] J. P. Berdahl, R. R. Allingham, D. H. Johnson, *Cerebrospinal fluid pressure is decreased in primary open-angle glaucoma*, Ophthalmology 115(5) (2008) 763-8.

[3] D. Fleischman, R. R. Allingham, *The role of cerebrospinal fluid pressure in glaucoma and other ophthalmic diseases: A review*, Saudi J Ophthalmol 27(2) (2013) 97-106

[4] A. J. Feola, B. Coudrillier, J. Mulvihill, D. M. Geraldes, N. T. Vo, J. Albon, R. L. Abel, B. C. Samuels, C. R. Ethier, *Deformation of the Lamina Cribrosa and Optic Nerve Due to Changes in Cerebrospinal Fluid Pressure*, Invest Ophthalmol Vis Sci 58(4) (2017) 2070-2078.

[5] A. J. Feola, B. Coudrillier, J. Mulvihill, D. M. Geraldes, N. T. Vo, J. Albon, R. L. Abel, B. C. Samuels, C. R. Ethier, *Deformation of the Lamina Cribrosa and Optic Nerve Due to Changes in Cerebrospinal Fluid Pressure*, Invest Ophthalmol Vis Sci 58(4) (2017) 2070-2078.

[6] W. H. Morgan, D. Y. Yu, V. A. Alder, S. J. Cringle, R. L. Cooper, P. H. House, I. J. Constable, *The correlation between cerebrospinal fluid pressure and retrolaminar tissue pressure*, Invest Ophthalmol Vis Sci 39(8) (1998) 1419-28.

[7] J. P. Berdahl, M. P. Fautsch, S. S. Stinnett, R. R. Allingham, *Intracranial pressure in primary open angle glaucoma, normal tension glaucoma, and ocular hypertension: a case-control study*, Invest Ophthalmol Vis Sci 49(12) (2008) 5412-8.

[8] W. H. Morgan, B. C. Chauhan, D. Y. Yu, S. J. Cringle, V. A. Alder, P. H. House, *Optic disc movement with variations in intraocular and cerebrospinal fluid pressure*, Invest Ophthalmol Vis Sci 43(10) (2002) 3236-42.

[9] Yang D, Fu J, Hou R, Liu K, Jonas J B, Wang H, Chen W, Li Z, Sang J, Zhang Z, Liu S, Cao Y, Xie X, Ren R, Lu Q, Weinreb R N, Wang N, *Optic neuropathy induced by experimentally reduced cerebrospinal fluid pressure in monkeys*, Invest Ophthalmol Vis Sci. 2014 Apr. 15; 55(5): 3067-73.

The invention claimed is:

1. A device for use in modeling ocular translaminar pressure gradients, the device comprising:
   a base having a first end and a second end, the base defining:
      a recess extending from the first end to a bottom defined between the first and second ends; and
      a protrusion extending upward from the bottom of the recess to an upper end of the protrusion, the upper end of the protrusion disposed between the bottom of the recess and the first end of the base, and the upper end of the protrusion sized to receive a donor eye cup over the upper end of the protrusion;
      where the base defines at least one fluid port extending through the upper end of the protrusion;
   an annular retainer configured to fit around the protrusion and to be coupled to the base such that a donor eye cup disposed between the annular retainer and the base and over the upper end of the protrusion is secured between the annular retainer and the base and an interface between the so disposed donor eye cup and the protrusion is sealed; and
   a lid having a first side, a second side configured to face the first end of the base, and an annular sidewall on the second side, the annular sidewall defining a chamber and having a distal end that encircles an open end of the chamber, the distal end of the annular sidewall configured such that when the lid is secured relative to the first end of the base and the distal end of the annular sidewall extends into the recess of the base, a donor eye cup secured between the annular retainer and the base is also secured between the annular sidewall and the protrusion, and an interface between the annular sidewall and the so secured donor eye cup is sealed, where the lid defines at least one fluid port in fluid communication with the chamber.

2. The device of claim 1, where the donor eye cup is a posterior human eye cup.

3. The device of claim 1, where the distal end of the protrusion of the base is hemispherical.

4. The device of claim 1, where the protrusion of the base has a circular cross-section.

5. The device of claim 4, where the recess around the protrusion defines an annular space sized to receive the annular retainer.

6. The device of claim 4, where an inner diameter of the annular sidewall of the lid is smaller than a diameter of the protrusion of the base.

7. The device of claim 6, where when the lid is secured relative to the base, a minimum distance between the upper end of the protrusion of the base and the distal end of the annular sidewall of the lid is greater than zero but smaller than a thickness of a wall of an adult human donor eye cup.

8. The device of claim 1, where the base defines two fluid ports extending through the upper end of the protrusion, and the lid defines two fluid ports in fluid communication with the chamber.

9. The device of claim 1, where the base defines a first fluid port extending through the upper end of the protrusion and a second fluid port extending below the upper end of the protrusion, and the lid defines two fluid ports in fluid communication with the chamber.

10. The device of claim 1, where the annular retainer defines one or more annular grooves each configured to receive an O-ring.

11. The device of claim 1, where the lid is substantially square-shaped, and where the base is substantially square-shaped.

12. The device of claim 1, where the chamber includes an insert disposed at a particular angle from an axis through the protrusion, the axis being perpendicular to the second end of the base.

13. The device of claim 12, where the particular angle is between substantially 6 degrees and substantially 10 degrees.

14. A system for modeling ocular translaminar pressure gradients, the system comprising:
   a device of claim 1;
   a first source of fluid pressure in fluid communication with the at least one fluid port of the base; and
   a second source of fluid pressure in fluid communication with the at least one fluid port of the lid.

15. The system of claim 14, where the base defines two fluid ports extending through the upper end of the protrusion, and the lid defines two fluid ports in fluid communication with the chamber, the first source of fluid pressure is coupled to a first one of the fluid ports of the base, the second source of fluid pressure is coupled to a first one of the fluid ports of the lid, and the system further comprises:
- a first pressure transducer coupled to a second one of the fluid ports of the base; and
- a second pressure transducer coupled to a second one of the fluid ports of the lid.

16. The system of claim 14, further comprising a control device configured to initiate adjustment of the first source of fluid pressure, the second source of fluid pressure, or both.

17. A method for modeling ocular translaminar pressure gradients, using a device of claim 1 having a donor eye cup secured between the annular retainer and the base and the lid coupled to the base, the method comprising:
- adjusting a fluid pressure gradient between a first fluid pressure in the at least one fluid port of the base and a second fluid pressure in the at least one fluid port of the lid, and thereby adjusting a corresponding fluid pressure gradient between the first fluid pressure on one side of the donor eye cup between the donor eye cup and the protrusion and the second fluid pressure on the other side of the donor eye cup in the chamber of the lid.

18. The method of claim 17, further comprising:
- varying the fluid pressure gradient over time.

19. The method of claim 17, where adjusting the fluid pressure gradient involves adjusting one or both of the heights of first and second fluid reservoirs relative to one another, the first and second fluid reservoirs respectively coupled to the fluid ports of the base and the lid.

20. The method of claim 17, where the base defines two fluid ports extending through the upper end of the protrusion, and the lid defines two fluid ports in fluid communication with the chamber, a first source of fluid pressure is coupled to a first one of the fluid ports of the base, a second source of fluid pressure is coupled to a first one of the fluid ports of the lid, and the method further comprises:
- measuring the first fluid pressure with a first pressure transducer coupled to a second one of the fluid ports of the base; and
- measuring the second fluid pressure with a second pressure transducer coupled to a second one of the fluid ports of the lid.

* * * * *